United States Patent
Fiorini Puybaret et al.

(10) Patent No.: US 11,207,265 B2
(45) Date of Patent: Dec. 28, 2021

(54) **EXTRACT OF THE AERIAL PARTS OF *LAWSONIA INERMIS* AND ITS PREPARATION METHOD**

(71) Applicant: PIERRE FABRE DERMO-COSMETIQUE, Boulogne-Billancourt (FR)

(72) Inventors: Christel Fiorini Puybaret, Toulouse (FR); Philippe Joulia, Villenouvelle (FR); Laurent Subra, Montgaillard (FR)

(73) Assignee: PIERRE FABRE DERMO-COSMEFIQUE, Boulogne-Billancourt (FR)

( * ) Notice: Subject to any disclaimer, the term of this patent is extended or adjusted under 35 U.S.C. 154(b) by 0 days.

(21) Appl. No.: 16/769,003

(22) PCT Filed: Dec. 12, 2018

(86) PCT No.: PCT/EP2018/084641
§ 371 (c)(1),
(2) Date: Jun. 2, 2020

(87) PCT Pub. No.: WO2019/115651
PCT Pub. Date: Jun. 20, 2019

(65) Prior Publication Data
US 2020/0330365 A1    Oct. 22, 2020

(30) Foreign Application Priority Data
Dec. 12, 2017   (FR) ........................ 1762019

(51) Int. Cl.
*A61Q 5/10*    (2006.01)
*A61K 8/9789*  (2017.01)

(52) U.S. Cl.
CPC .............. *A61K 8/9789* (2017.08); *A61Q 5/10* (2013.01)

(58) Field of Classification Search
CPC .. A61Q 5/10; A61K 2800/4324; A61K 8/365; A61K 8/35; A61K 8/922;
(Continued)

(56) References Cited

U.S. PATENT DOCUMENTS 4,190,064 A * 2/1980 Gordon ................ A61K 8/9789
                                                    132/208
5,447,538 A * 9/1995 Rosenbaum ......... A61K 8/9789
                                                    8/405
(Continued)

FOREIGN PATENT DOCUMENTS

DE    19838809 A1    3/2000
FR    2473310 A1     7/1981

OTHER PUBLICATIONS

Draelos, "Sunscreens and Hair Photoprotection", Dermatol Clin, 2006, vol. 24, pp. 81-84 (4 pages).
(Continued)

*Primary Examiner* — Eisa B Elhilo
(74) *Attorney, Agent, or Firm* — Birch, Stewart, Kolasch & Birch, LLP

(57) ABSTRACT

The invention relates to an extract of the aerial parts of *Lawsonia inermis*, as well as its preparation method and the extract that can be obtained by said method. The invention also relates to a cosmetic dye composition comprising such an extract. The invention finally concerns a cosmetic method for dying keratin fibers comprising the application of such a composition.

18 Claims, 25 Drawing Sheets

(58) Field of Classification Search
CPC .......... A61K 8/64; A61K 8/355; A61K 8/645; A61K 2236/31; A61K 2236/51
USPC ............................................................ 8/405
See application file for complete search history.

(56) References Cited

U.S. PATENT DOCUMENTS

2007/0251024 A1* 11/2007 Greaves ............... A61K 8/9789
    8/405
2009/0249563 A1* 10/2009 Greaves ................ A61K 8/365
    8/405

OTHER PUBLICATIONS

French preliminary Search Report, dated Feb. 28, 2018, for French Application No. 845986.

Gallo et al., "Henna through the centuries: a quick HPTLC analysis proposal to check henna identity", Rev Bras Famacogn, 2014, vol. 24, pp. 133-140 (9 pages).

Huh et al., "A cell-based system for screening hair growth-promoting agents", Arch Dermatrol Res, 2009 (published online Mar. 11, 2009), vol. 301, pp. 381-385 (6 pages).

Nichols et al., "Skin photoprotection by natural polyphenols: anti-inflammatory, antioxidant and DNA repair mechanisms", Arch Dermatrol Res, 2010 (publised online Nov. 7, 2009), vol. 302, pp. 71-83 (13 pages).

Romanová et al., "Study of antioxidant effect of apigenin, luteolin and quercetin by DNA protective method*", Neoplasma, 2001, vol. 48, No. 2, pp. 104-107 (4 pages).

Saewan et al., "Photoprotection of natural flavonoids", Journal of Applied Pharmaceutical Science, Sep. 2013, vol. 3, No. 9, pp. 129-141 (13 pages).

Scientific Committee on Consumer Safety, "Opinion on *Lawsonia inermis* (Henna) COLIPA No. C169", Plenary Meeting, Sep. 19, 2013, pp. 1-44.

Wang et al., "Rapid determination of para-phenylenediamine by gas chromatography—mass spectometry with selected ion monitoring in henna—containing cosmetic products", Journal of Chromatography B, 2011 (published online May 6, 2011) vol. 879, pp. 1795-1801 (7 pages).

Written Opinion of the International Searching Authority, and International Search Report, dated Apr. 8, 2019, for International Application No. PCT/EP2018/084641.

* cited by examiner

EXTRACT OF THE AERIAL PARTS OF *LAWSONIA INERMIS* AND ITS PREPARATION METHOD

The invention relates to an extract of the aerial parts of *Lawsonia inermis*, as well as its preparation method and the extract that can be obtained by said method. The invention also relates to a cosmetic dye composition comprising such an extract. The invention finally concerns a cosmetic method for dying keratin fibers comprising the application of such a composition.

*Lawsonia inermis*, commonly called henna, belongs to the Lythraceae family. This shrub, which can reach a height of 6 meters, grows naturally in the tropical and subtropical regions of Africa and Asia, notably. It has a gray bark, dense branching, and quadrangular and thorny branches on the oldest ones. Its leaves grow opposite each other and are simple and whole. The scented white or red flowers are grouped in large pyramidal panicles of 25 cm long.

Henna leaves, which produce red and orange tints, have been used for more than 5000 years for dying hair and skin, or even textile dying.

Their dye properties are due to lawsone (2-hydroxy-1,4-naphthoquinone), which reacts with the keratin present in the skin or nails by a Michael addition.

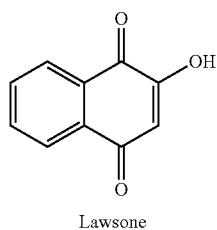 [SMILES: O=C1C=C(O)C(=O)c2ccccc21]

Lawsone

Generally, lawsone is able to undergo this type of condensation with various compounds containing an amino group, such as proteins, peptides or amino acids. This is why the commercially-available henna extracts have a relatively low lawsone content, which also decreases quickly over time.

Moreover, the quantity of lawsone found in the free state in *Lawsonia inermis* leaves is actually very small. In fact, it is predominantly present in the form of heterosides [Gallo et al. *Rev. Bras. Pharmacogn.* 2014, 23, 133-140; COLIPA no. C169, 2013].

Hennosides A, B and C, which are monoglycosylated lawsone derivatives, have notably been identified.

Hydrolysis of these precursors, followed by autooxidation of the resulting aglycone, leads to the formation of lawsone according to the reaction scheme indicated below.

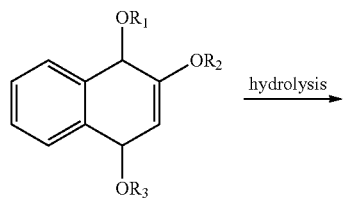
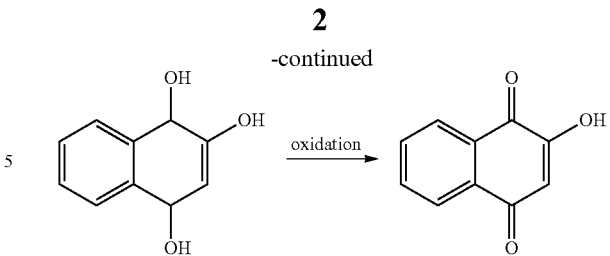

$R_1$=glucose, $R_2$=$R_3$=H;

$R_2$=glucose; $R_1$=$R_3$=H; or $R_3$=glucose; $R_1$=$R_2$=H.

Thus, a number of known extraction processes for *Lawsonia inermis* include a step in acidic medium, typically at a pH comprised between 1 and 3, during which the hennosides are hydrolyzed.

An extraction process is notably described in document FR2473310.

The inventors of the present invention have been able to develop an extraction process for *Lawsonia inermis* allowing an extract with a high lawsone content to be obtained by implementing enzymatic hydrolysis of the glycosylated lawsone derivatives. Said extract is also distinguished by its stability over time.

The present invention is part of a desire to set up synthesis pathways that are greener and that allow claiming that the active ingredients thus obtained are natural.

Therefore, the solvent(s) used in the present invention will preferably be natural solvents and/or of natural origin from renewable resources, as opposed to fossil resources, these solvents advantageously being obtainable by processes that respect the environment. The extract thus obtained according to the method of the invention, will therefore be a natural extract and/or of natural origin, coming from renewable resources, as opposed to fossil resources.

The invention thus relates to an extract of the aerial parts of *Lawsonia inermis* containing between 10 and 60% by weight of lawsone relative to the total weight of the dry extract, characterized in that the lawsone notably results from enzymatic hydrolysis of glycosylated lawsone derivatives, such as hennosides. Preferably, said extract is also characterized in that the lawsone content is stable over time.

"Aerial parts" means the parts of the plant located above the ground, for example, leaves, petioles, flowers, seeds and branches, in particular leaves, branches and petioles, or a mix thereof, preferably leaves, branches or a mix thereof.

Advantageously, the extract according to the invention is an extract of leaves and/or branches of *Lawsonia inermis*.

"Dry extract" intends to refer, within the meaning of the present invention, to an extract with no extraction solvent or medium, or containing them only in insignificant traces. Such a dry extract thus contains only the material coming from *Lawsonia inermis*.

"Glycosylated lawsone derivatives", also called lawsone glycosides or heterosides, means, within the framework of the present invention, any compound of general formula (I) below:

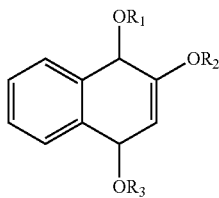
(I)

wherein $R_1$, $R_2$ and $R_3$ represent, independently of one another, H or a sugar, such as glucose, at least one of $R_1$ to $R_3$ being different from H,
for which hydrolysis of the glycoside bond(s) leads to the formation of aglycone which undergoes an autooxidation reaction to form lawsone.

In particular, hennosides A, B and C are glycosylated lawsone derivatives.

"Enzymatic hydrolysis" is, in the context of the present invention, a hydrolysis reaction catalyzed by an enzyme, which can be an endogenous *Lawsonia inermis* enzyme or from an exogenous source, preferably an endogenous *Lawsonia inermis* enzyme, it being understood that said enzyme is a glucosidase, such as a β-glucosidase [Gallo et al.], whose action leads to breaking the glucoside bonds of the glycosylated lawsone derivatives.

Within the scope of the present invention, the lawsone content of an extract according to the invention is considered to be "stable over time" if the quantity of lawsone initially present in the extract does not decrease by more than 40%, in particular not more than 30%, preferably not more than 20%, notably not more than 15%, advantageously not more than 10% in 1 month at room temperature (15° C.-25° C.), with a relative humidity (RH) of 60%, and protected from light. The room temperature values are those defined in the European Pharmacopoeia.

In one particular embodiment, the lawsone content of an extract according to the invention does not decrease by more than 40%, in particular not more than 30%, preferably not more than 20% in 3 months under the previously enumerated conditions.

In particular, the lawsone content of an extract according to the invention does not decrease by more than 10% in 3 months under the previously enumerated conditions.

Advantageously, the lawsone content of an extract according to the invention does not decrease by more than 40%, preferably not more than 30%, more preferably not more than 20% in 6 months under the previously enumerated conditions.

In particular, the lawsone content of an extract according to the invention does not decrease by more than 10% in 6 months under the previously enumerated conditions.

Preferably, the lawsone content of an extract according to the invention does not decrease by more than 40%, particularly not more than 30%, more particularly not more than 20% in 12 months at room temperature under the previously enumerated conditions.

In particular, the lawsone content of an extract according to the invention does not decrease by more than 10% in 12 months at room temperature under the previously enumerated conditions.

The stability of an extract according to the invention may also be evaluated under so-called accelerated stability conditions. These conditions are a temperature of 40° C. (±2) and an RH of 75% (±5). The lawsone content of an extract according to the invention is evaluated as being "stable over time" under accelerated stability conditions if the quantity of lawsone initially present in the extract does not decrease by more than 40%, preferably not more than 30%, particularly not more than 20%, notably not more than 15%, advantageously not more than 10% in 1 month.

Advantageously, the lawsone content of an extract according to the invention does not decrease by more than 40%, particularly not more than 30%, more particularly not more than 20% in 3 months under the previously enumerated accelerated stability conditions.

In particular, the lawsone content of an extract according to the invention does not decrease by more than 40%, particularly not more than 30%, more particularly not more than 20%, notably not more than 10% in 6 months under the previously enumerated accelerated stability conditions.

In one particular embodiment, the extract according to the invention contains between 10% and 50%, in particular between 15% and 40% by weight of lawsone relative to the total weight of the dry extract.

Advantageously, the extract according to the invention contains at least 15%, preferably at least 20%, more advantageously at least 25% by weight of lawsone relative to the total weight of the dry extract; the percentages being expressed relative to the total weight of the dry extract (before any addition of a drying carrier).

The lawsone content can notably be determined according to the HPLC assay method described after the examples (Method 1).

In one embodiment, an extract according to the invention does not contain more than 2%, preferably not more than 1.5%, notably not more than 1% by weight of proteins, peptides or amino acids relative to the total weight of the dry extract.

The free amino acids, peptides and proteins can notably be assayed by ninhydrin spectrophotometry, according to the method described after the examples (Method 2).

In one embodiment, an extract according to the invention also comprises chlorophylls, notably chlorophyll a and/or chlorophyll b, the total chlorophyll content being less than 25% by weight relative to the total weight of the dry extract, notably less than 20% by weight, advantageously less than 10% by weight relative to the dry extract.

In one particular embodiment, the extract according to the invention does not contain more than 5%, preferably not more than 2% by weight of chlorophylls relative to the total weight of the dry extract. Advantageously, the extract according to the invention does not contain chlorophyll.

The chlorophylls can notably be assayed by weight assay according to the method described after the examples (Method 3).

An extract according to the invention may also contain any compound naturally present in the aerial parts of *Lawsonia inermis*, notably the leaves and or branches of *Lawsonia inermis*.

In particular, an extract according to the invention also contains phenol compounds, such as gallic acid, para-coumaric acid, 2,3,4,6-tetrahydroxyacetophenone and 3,4,5-trihydroxyacetophenone; flavonoids, such as luteolin, apigenin, catechin, 3',4',5,7-tetrahydroxyflavanone, 3',5,7-trihydroxy-4'-methylflavone; sterols, such as β-sitosterol, triterpenes, such as lupeol; and/or heterosides thereof, such as lalioside, myrciaphenone A, 1,2-dihydroxy-4-O-glycosyloxynaphtalene (also called 4-O-β-D-glucopyranoside), luteolin-4'-O-glucoside, apigenin-7-O-β-glucoside, luteolin-3'-O-glucoside and apigenin-4'-O-β-glucoside.

More particularly, an extract according to the invention also contains phenol compounds, such as gallic acid, para-coumaric acid, 2,3,4,6-tetrahydroxyacetophenone and 3,4,5-trihydroxyacetophenone; flavonoids, such as luteolin, apigenin, catechin, 3',4',5,7-tetrahydroxyflavanone, 3',5,7-trihydroxy-4'-methylflavone; and/or heterosides thereof, such as lalioside, myrciaphenone A, 1,2-dihydroxy-4-O-glycosyloxynaphtalene, luteolin-4'-O-glucoside, apigenin-7-O-β-glucoside, luteolin-3'-O-glucoside and apigenin-4'-O-β-glucoside.

The chemical structures of the above specific compounds are indicated in the following Table 1:

TABLE 1 compounds potentially present in the extract of the invention

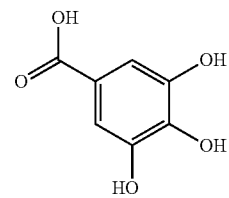

Chemical Formula: $C_7H_6O_5$
Molecular Weight: 170.1200
gallic acid

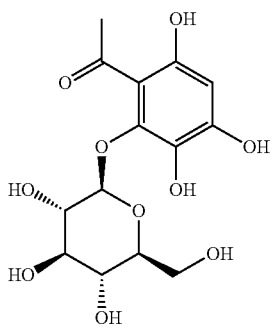

Chemical Formula: $C_{14}H_{18}O_{10}$
Molecular Weight: 346.2880
lalioside

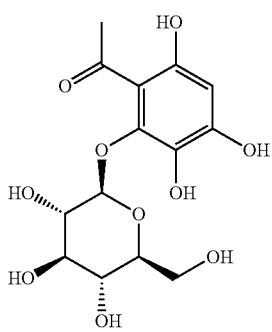

Chemical Formula: $C_{14}H_{18}O_9$
Molecular Weight: 330.2890
myrciaphenone A

TABLE 1-continued compounds potentially present in the extract of the invention

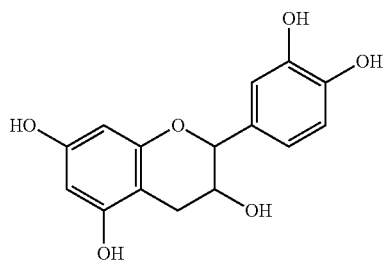

Chemical Formula: $C_{15}H_{14}O_6$
Molecular Weight: 290.2710
catechin

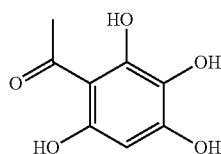

Chemical Formula: $C_8H_8O_5$
Molecular Weight: 184.1470
2,3,4,6-tetrahydroxyacetophenone

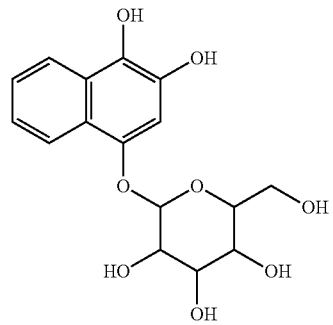

Chemical Formula: $C_{16}H_{18}O_8$
Molecular Weight: 338.3120
1,2-dihydroxy-4-O-glycosyloxynaphtalene

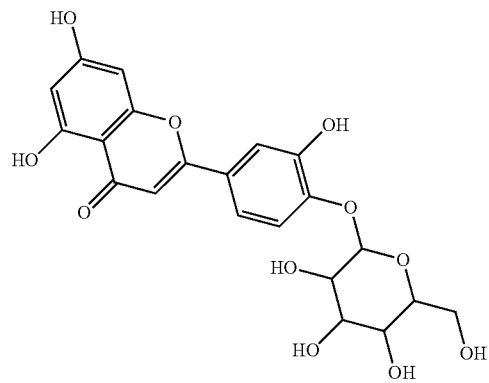

Chemical Formula: $C_{21}H_{20}O_{11}$
Molecular Weight: 448.3800
luteolin-4'-O-glucoside TABLE 1-continued compounds potentially present in the extract of the invention

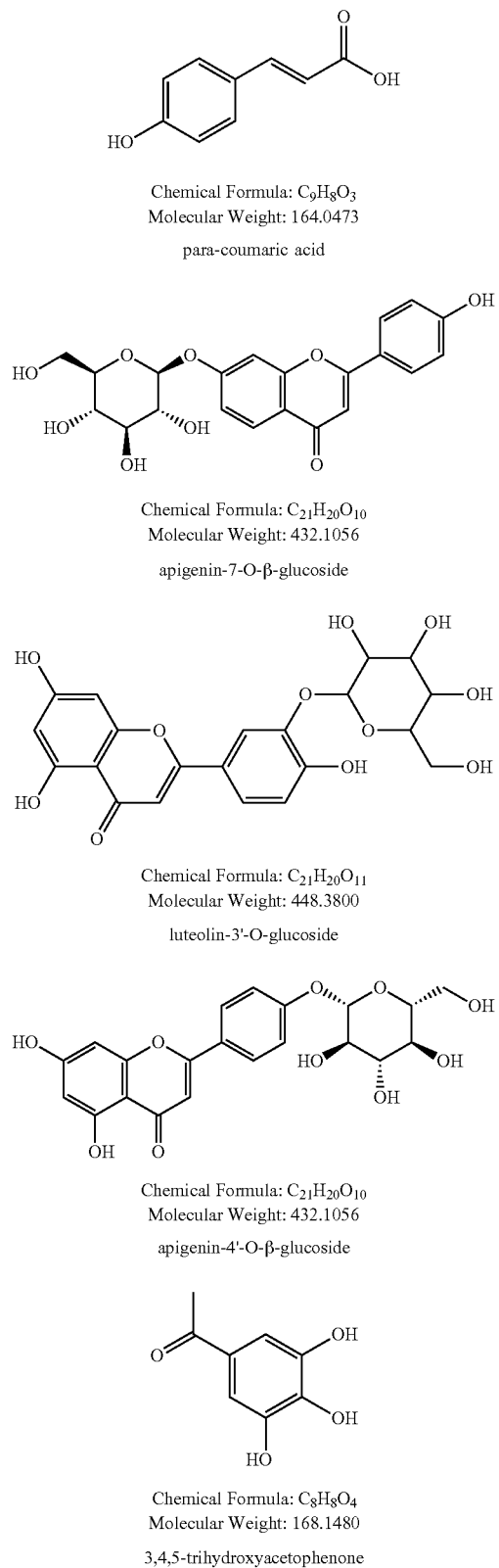

Chemical Formula: C$_9$H$_8$O$_3$
Molecular Weight: 164.0473 para-coumaric acid

Chemical Formula: C$_{21}$H$_{20}$O$_{10}$
Molecular Weight: 432.1056 apigenin-7-O-β-glucoside

Chemical Formula: C$_{21}$H$_{20}$O$_{11}$
Molecular Weight: 448.3800 luteolin-3'-O-glucoside

Chemical Formula: C$_{21}$H$_{20}$O$_{10}$
Molecular Weight: 432.1056 apigenin-4'-O-β-glucoside

Chemical Formula: C$_8$H$_8$O$_4$
Molecular Weight: 168.1480

3,4,5-trihydroxyacetophenone

TABLE 1-continued compounds potentially present in the extract of the invention

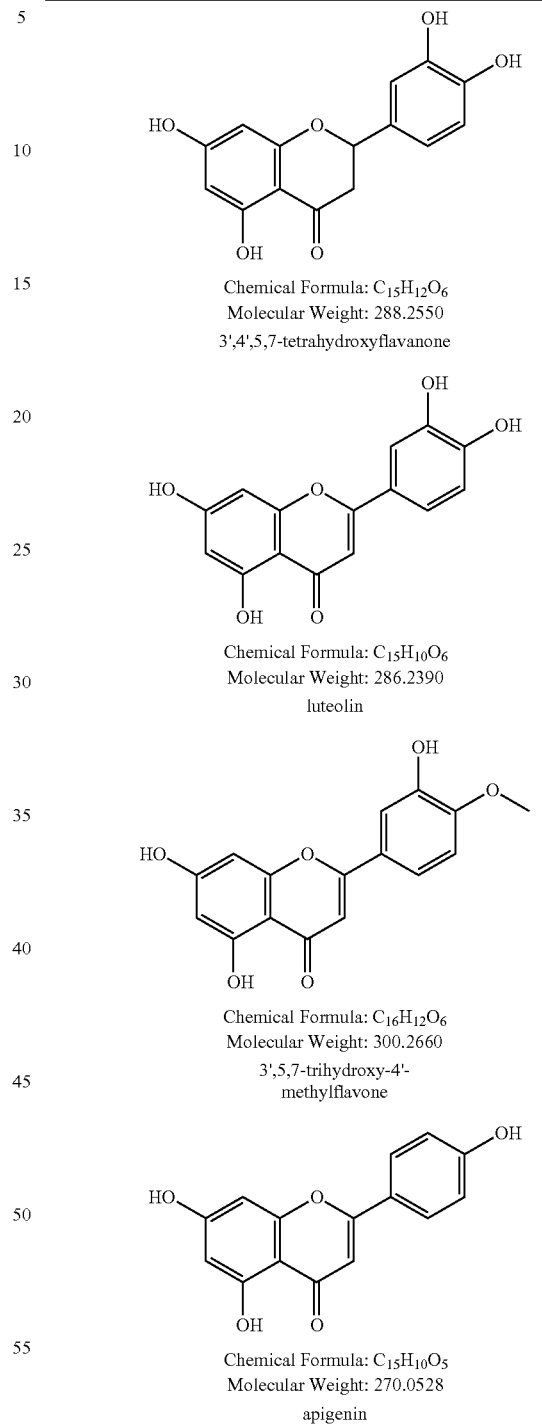

Chemical Formula: C$_{15}$H$_{12}$O$_6$
Molecular Weight: 288.2550

3',4',5,7-tetrahydroxyflavanone

Chemical Formula: C$_{15}$H$_{10}$O$_6$
Molecular Weight: 286.2390 luteolin

Chemical Formula: C$_{16}$H$_{12}$O$_6$
Molecular Weight: 300.2660

3',5,7-trihydroxy-4'-methylflavone

Chemical Formula: C$_{15}$H$_{10}$O$_5$
Molecular Weight: 270.0528 apigenin

Flavonoids, such as luteolin and apigenin have many interesting biological properties, such as free radical scavenging and antioxidative effects [Romanov et al., *Neoplasma* 2001, 48(2), 104-107] as well as anti-inflammatory activity, which, combined with their capacity to absorb UV light, are responsible for their ability to provide protection from UV radiation [Saewan et al., *JAPS* 2013, 3(9), 129-141]. Although the hair photoprotection is a topic that is not commonly addressed, the chemical effects of UV radiation and their impact on the hair shaft should not be neglected [Draelos, *Dermatol. Clin.* 2006, 24, 81-84]. Therefore, the presence of compounds that have a photoprotective effect in a cosmetic composition intended for hair dyeing is of particular interest.

Luteolin and apigenin are also well-known natural dyes, that can be used for coulouring hair and textiles.

Besides, it has been shown that apigenin is a hair-growth-promoting agent [Huh et al. *Arch. Dermatol. Res.,* 2009, 301, 381-385].

Polyphenols, such as 2,3,4,6-tetrahydroxyacetophenone, and phenolic acids, such as para-coumaric acid, also have antioxidant and photoprotective properties [Nichols et al., *Arch. Dermatol. Res.* 2010, 302, 71-83].

The invention thus relates more particularly to an extract of the aerial parts of *Lawsonia inermis* as described above, containing between 10 and 60% by weight of lawsone relative to the total weight of the dry extract, wherein the lawsone notably results from enzymatic hydrolysis of glycosylated lawsone derivatives, such as hennosides, said extract also containing luteolin, apigenin and para-coumaric acid.

The extract according to the invention may further contain 2,3,4,6-tetrahydroxyacetophenone, and optionally 3,4,5-trihydroxyacetophenone and 1,2-dihydroxy-4-O-glycosyloxynaphtalene.

The invention also relates to an extract of the aerial parts of *Lawsonia inermis* as described above containing between 10 and 60% by weight of lawsone relative to the total weight of the dry extract, wherein the lawsone notably results from enzymatic hydrolysis of glycosylated lawsone derivatives, such as hennosides, said extract also containing 2,3,4,6-tetrahydroxyacetophenone.

In one embodiment, the extract according to the invention may be in the dry extract form, advantageously in powder form.

In one embodiment, the extract according to the invention may be a standardized extract.

"Standardized extract" means an extract having a chosen lawsone content, such as, for a cosmetic application for instance, a lawsone content comprised between 0.6% and 1.4%, in particular approximately 1.3% by weight of lawsone relative to the total weight of the dry extract.

This lawsone content may be obtained by the addition of a carrier, chosen from among protein-free carriers alone or in mixture.

Said "carrier" must be inert vis-à-vis the extract and its components: it does not interact with the extract nor its components, more particularly with lawsone, contributes to its protection and allows to standardize the final content of the active extract or molecule. It must be "cosmetically-acceptable", which means, in the context of the present invention, that it is useful in the preparation of a cosmetic composition, and generally safe, non-toxic and neither biologically nor otherwise undesirable, and that is acceptable for a cosmetic use, notably by topical application.

The carrier can notably be chosen from among propanediol, pentanediol, glycerine, propylene glycol, methyl THF and amylic alcohol.

A dry extract according to the invention can also be standardized.

For dry extracts, the carrier may act as a support during the drying of the extract, and is preferably chosen from among sugars and polysaccharide derivatives, such as fructose, glucose, sucrose, maltodextrins, cellulose derivatives, starch, notably maize, wheat or rice starch, agar-agar, gums, mucilages; and polyols such as mannitol, sorbitol, xylitol, etc. In particular, it is selected from fructose, maltodextrins and starch, notably rice starch.

Within the framework of the present invention, the carrier is preferably a natural carrier and/or of natural origin from renewable resources, as opposed to fossil resources, these carriers advantageously being obtainable by processes that respect the environment.

The invention thus relates more particularly to a standardized dry extract of aerial parts of *Lawsonia inermis* containing between 0.6 and 1.4 wt. % of lawsone, and further containing luteolin, apigenin and para-coumaric acid.

The standardized dry extract according to the invention may further contain 2,3,4,6-tetrahydroxyacetophenone, and optionally 3,4,5-trihydroxyacetophenone and 1,2-dihydroxy-4-O-glycosyloxynaphtalene.

It may also contain any compound listed in Table 1.

In particular, the standardized dry extract according to the invention is such that:

the luteolin content is comprised between 0.05 and 1.0 wt. %, the apigenin content is comprised between 0.01 and 0.5 wt. %, and the para-coumaric acid content is comprised between 0.01 and 0.5 wt. %.

In one embodiment, the standardized dry extract according to the invention further contains 2,3,4,6-tetrahydroxyacetophenone in a content comprised between 0.05 and 4 wt. %, notably between 0.1 and 2 wt. %, in particular between 0.4 and 1.2 wt. %.

The invention also relates more particularly to a standardized dry extract of aerial parts of *Lawsonia inermis* containing between 0.6 and 1.4 wt. % of lawsone, and further containing 2,3,4,6-tetrahydroxyacetophenone.

In one embodiment, the 2,3,4,6-tetrahydroxyacetophenone content is comprised 0.05 and 4 wt. %, notably between 0.1 and 2 wt. %, in particular between 0.4 and 1.2 wt. %.

Preferably, the standardized dry extract complies with the specifications defined previously regarding the stability of the lawsone content over time.

Thus, after 1 month, 3 months, 6 months or 12 months at room temperature (15° C.-25° C.), with a relative humidity (RH) of 60%, and protected from light, the lawsone content does not decrease by more than 40%, preferably not more than 30%, in particular not more than 20%, notably not more than 15%, advantageously not more than 10%, more advantageously not more than 5%.

The stability of the standardized dry extract extract according to the invention may also be evaluated accelerated stability conditions.

Thus, after 1 month, 3 months or 6 months at 40° C. (±2° C.), with a relative humidity (RH) of 75% (±5%), the lawsone content does not decrease by more than 40%, preferably not more than 30%, in particular not more than 20%, notably not more than 15%, advantageously not more than 10%, more advantageously not more than 5%.

In one embodiment, the standardized dry extract of the invention contains at least 80%, advantageously at least 90%, notably at least 92%, in particular at least 95% by weight of carrier, relative to the total weight of the standardized dry extract.

The invention also relates to a preparation method for a lawsone extract comprising the following steps:

a) maceration of the aerial parts of *Lawsonia inermis* in water, during which the glycosylated lawsone derivatives, such as hennosides, initially present in the aerial parts of *Lawsonia inermis* are partially or totally hydrolyzed enzymatically, leading to an aqueous solution containing lawsone;

b) addition of an organic solvent to the solution obtained from step a), the miscibility with water of said solvent being less than 10%, advantageously 5% by weight at 25° C., the miscibility of said solvent in water being less than 10%, advantageously 5% by weight at 25° C., leading to the formation of an aqueous phase and an organic phase;

c) recovery of the organic phase obtained from step b); and d) concentration of the organic phase recovered from step c), allowing obtaining a lawsone-rich extract.

"Lawsone-rich extract" means, in the context of the present invention, an extract containing between 10% and 60% by weight, notably between 10% and 50%, in particular between 15% and 40% by weight of lawsone relative to the total weight of the dry extract.

Advantageously, said extract according to the invention contains at least 15%, preferably at least 20%, more advantageously at least 25% by weight of lawsone relative to the total weight of the dry extract; (before any addition of a drying carrier).

Advantageously, the lawsone-rich extract obtained from step d) contains more than 50%, notably more than 60%, advantageously more than 70% of the lawsone initially present in the free form or in the form of glycosylated lawsone derivatives, such as hennosides, in the aerial parts of *Lawsonia inermis* subjected to maceration in step a).

The quantity of lawsone initially present in the free form or in the form glycosylated lawsone derivatives in the aerial parts of *Lawsonia inermis* subjected to maceration in step a) is also called "lawsone potential of the plant".

In one preferred embodiment according to the invention, the lawsone-rich extract obtained from step d) contains between 50% and 90%, notably between 60% and 90%, in particular between 70% and 90% of the lawsone potential of the plant.

The lawsone potential of the plant can notably be determined according to the HPLC assay method described after the examples (Method 1).

In particular, the aerial parts of *Lawsonia inermis* subject to maceration in step a) are leaves, which can be fresh or dried, preferably dried, branches or a mixture of the two.

Step a) is preferably conducted at a temperature comprised between 20° C. and 60° C., notably between 20° C. and 50° C., in particular between 25° C. and 45° C., more particularly between 30° C. and 45° C., typically 40° C.

It is understood that step a) is conducted at a pH permitting the enzyme or enzymes that catalyze the hydrolysis of the glycosylated lawsone derivatives to function. In particular, step a) is conducted at a pH comprised between 4 and 8, preferably between 5 and 7.5, advantageously between 5.5 and 7.5, typically at neutral pH.

"Neutral pH" means a pH comprised between 6.5 and 7.5, particularly around 7.

Advantageously, step a) is carried out under stirring. Stirring may be obtained by any of the methods well known to the person skilled in the art.

The duration of maceration is advantageously comprised between 15 minutes and 2 h, in particular between 15 minutes and 1 h, advantageously it is approximately 30 minutes.

During step a), the volume of water used is 5 to 15 times greater, advantageously 6 to 10 times greater, typically 10 times greater than the mass of the aerial parts of *Lawsonia inermis* subjected to maceration. Thus, when the method according to the invention is implemented on 100 g of the aerial parts of *Lawsonia inermis*, the volume of water used during step a) is comprised between 500 mL and 1500 mL, advantageously between 600 mL and 1000 mL, typically 1000 mL.

It should be noted that the whole mixture resulting from step a), namely the plant material as well as the aqueous solution, is retained for step b).

Step b) may be done in batch or continuous mode.

In one particular embodiment, step b) of the method according to the invention comprises the following 3 substeps:

b.1) the addition of an organic solvent to the aqueous solution obtained from step a), the miscibility of water in said solvent being less than 10%, advantageously 5% by weight at 25° C., the miscibility of said solvent in water being less than 10%, advantageously 5% by weight at 25° C., b.2) the stirring of the solution obtained from step b.1), the stirring duration being comprised between 15 minutes and 2 h, in particular between 15 minutes and 1 h; typically, the stirring duration is approximately 30 minutes, and b.3) the decantation of the mixture obtained from step b.2), until two distinct phases are obtained, i.e., an aqueous phase and an organic phase.

Thus, the succession of substeps b.1), b.2) and b.3) lead to the formation of an aqueous phase and an organic phase.

The volume of organic solvent added during step b), in particular during step b.1), is such that the volume ratio of said organic solvent added during b) to the volume of water used during step a) is comprised between 0.25 and 2; notably between 0.5 and 2, notably between 0.8 and 1.5, in particular between 1 and 1.3.

In one particular embodiment, the organic solvent added during step b), in particular during step b.1), of the method according to the invention is a weakly polar solvent. "Weakly polar" means a solvent characterized by a dipole moment less than 2.0 D.

It is understood that although weakly polar, said organic solvent does solubilize lawsone. Thus, the solubility of lawsone in the organic solvent added in b), in particular in step b.1), in said solvent is greater than 70%, notably greater than 80%, advantageously greater than 90% by weight at 25° C.; the percentages being expressed relative to the total weight of lawsone present in the aqueous solution containing lawsone obtained from step a).

According to one advantageous aspect, the organic solvent added during step b), in particular during step b.1), of the method according to the invention is chosen from among alcohols, chlorinated solvents, ketones, ethers, esters and their mixtures which verifies the following criteria of miscibility in water and miscibility of water in said organic solvent:

the miscibility of water in said organic solvent is less than 10%, advantageously than 5% by weight at 25° C., the miscibility of said organic solvent in water is less than 10%, advantageously than 5% by weight at 25° C., "Alcohol" means, in the context of the present invention, an $R_4$—OH compound in which $R_4$ is a ($C_1$-$C_6$) alkyl group.

"Chlorinated solvent" means, in the context of the present invention, an alkane, i.e., a saturated hydrocarbon, containing between 1 and 6 carbon atoms, notably between 1 and 3 carbon atoms, of which a part or all of the hydrogen atoms are replaced by chlorine atoms.

"Ketone" means, in the context of the present invention, an $R_5$—CO—$R_6$, compound in which $R_5$ and $R_6$ are identical or different ($C_1$-$C_6$) alkyl groups.

"Ether" means, in the context of the present invention, an $R_7$—O—$R_8$, compound in which $R_7$ and $R_8$ are identical or different ($C_1$-$C_6$) alkyl groups.

"Ester" means, in the context of the present invention, an $R_9$—COO—$R_{10}$, compound in which $R_9$ and $R_{10}$ are identical or different ($C_1$-$C_6$) alkyl groups. The ester may, in particular, be an acetate, i.e., a $CH_3COO$—$R_{10}$ compound.

"($C_1$-$C_6$) alkyl" group means, in the context of the present invention, a saturated, linear or branched hydrocarbon chain, advantageously comprising 1 to 6, preferably 1 to 4 carbon atoms. Examples include the following groups: methyl, ethyl, propyl, isopropyl, butyl, isobutyl, sec-butyl, tert-butyl, pentyl or hexyl.

The alcohols that satisfy the previously enumerated miscibility criteria notably include n-amylic alcohol, also called 1-pentanol. The chlorinated solvents that satisfy the previously enumerated miscibility criteria notably include dichloromethane and chloroform.

The ketones that satisfy the previously enumerated miscibility criteria notably include methyl isobutyl ketone, commonly called MIBK.

The ethers that satisfy the previously enumerated miscibility criteria notably include diethyl ether, diisopropyl ether, dibutyl ether and methyl tert-butyl ether.

The esters that satisfy the previously enumerated miscibility criteria notably include ($C_1$-$C_6$) alkyl acetates, such as ethyl acetate, isopropyl acetate, butyl acetate and isoamyl acetate.

In one particular embodiment of the invention, the organic solvent added in step b), in particular during step b.1), is a ($C_1$-$C_6$) alkyl acetate or a mixture of ($C_1$-$C_6$) alkyl acetates, preferably chosen from the group consisting of ethyl acetate, isopropyl acetate, butyl acetate, isoamyl acetate and mixtures thereof. In a particularly preferred manner, it is isopropyl acetate.

Step c) of the method according to the invention consists in the recovery of the organic phase obtained from step b).

As will be clear to the skilled person, it is possible to repeat step b) on the aqueous phase obtained in the previous iteration of said step b). The new organic phase thus obtained is then recovered (repeat of step c)) and combined with the one resulting from the preceding iteration of step b).

Thus, in a variant of the method according to the invention, step d) consists in a step d') of concentrating the combination of organic phases recovered from several iterations of step b) followed by step c).

In one embodiment, the method according to the present invention can contain an additional step e) of drying the lawsone-rich extract obtained from step d). At the end of said step e), the lawsone-rich extract obtained is a dry extract.

Drying step e) may be conducted according to methods well known to the skilled person. In particular, the drying step may be done by pallet dryer, atomization, microwaves, zeodration or lyophilization.

In one particular embodiment, the method according to the present invention comprises, in between steps c) and d), an additional step c') of adding a carrier as defined above, and step d) is followed by the above drying step e).

At the end of said step e), the lawsone-rich extract obtained is a standardized dry extract is thus obtained.

According to one preferred embodiment, the method according to the invention does not include any step of changing the pH of the aqueous solution or the aqueous phase by addition of acid or base.

In one particular embodiment, the method according to the invention also comprises a step of extracting pigments, also called decoloration step.

The pigments extracted during the decoloration step are notably chlorophylls. However, it is understood that lawsone is not part of the pigments that the decoloration step seeks to eliminate.

The pigment extraction step can notably be done with an organic solvent.

It is understood that said organic solvent does not solubilize lawsone well. Thus, the solubility of lawsone in the organic solvent step used for the decoloration step is less than 15%, notably less than 10%, advantageously less than 5% by weight at 25° C.; the percentages being expressed relative to the total weight of lawsone contained in the extract or the solution which is undergoing the decoloration step.

Preferably, lawsone is not soluble in the organic solvent used for the pigment extraction step.

Advantageously, said organic solvent is a saturated or unsaturated hydrocarbon.

"Saturated or unsaturated hydrocarbon" means a compound made up uniquely of hydrogen and carbon atoms.

In particular, said saturated hydrocarbon can be chosen from among pentane, hexane, heptane, nonane, decane and cyclohexane.

Said unsaturated hydrocarbon can notably be benzene.

Preferably, the extraction step for pigments like chlorophyll is done with heptane.

The pigment extraction step done with an organic solvent may consist in a liquid-liquid or liquid-solid extraction.

When it is a liquid-liquid extraction, said step is inserted between steps a) and b) of the method according to the invention.

Advantageously, the liquid-liquid extraction decoloration step using an organic solvent comprises the following 4 substeps:
i) the addition of said organic solvent to the aqueous solution obtained from step a),
ii) the stirring of the solution obtained from step i), the stirring duration being comprised between 15 minutes and 2 h, in particular between 15 minutes and 1 h, typically the stirring duration is approximately 30 minutes, and
iii) the decantation of the mixture obtained from step ii), until two distinct phases are obtained, i.e., an aqueous phase and an organic phase, and
iv) the elimination of the organic phase.

Step b) of the method is then implemented in the aqueous phase resulting from step iii).

When it is a question of liquid-solid extraction, this step follows drying step e) of the method according to the invention. Liquid-solid extraction may be done according to methods well known to the skilled person.

Alternatively, the decoloration step may be done using supercritical $CO_2$, with or without the addition of co-solvent, directly in the dry extract. The chlorophyll is entrained by the supercritical $CO_2$. The residue is the decolored dry extract.

In one particular embodiment, the method according to the invention also comprises a filtration step situated between step a) and b), in order to separate the aerial parts of *Lawsonia inermis* from the aqueous solution containing lawsone, or situated between step c) and d), in order to separate the residue of aerial parts of *Lawsonia inermis* from the organic phase recovered in step c).

In another particular embodiment, a pectinase-type enzyme may be added in step a).

The method according to the invention may also be applied to any other plant that contains lawsone, such as *Impatiens balsamina*. The skilled person will know how to adapt the method of the invention to the plant in question. Thus, in the case of *Impatiens balsamina*, the skilled person will do an extraction of the roots, the parts of *Impatiens balsamina* richest in lawsone.

The present invention also relates to an extract that can be obtained by the method mentioned above. Such an extract complies with the specifications defined previously.

In particular, said extract contains between 10% and 60% by weight, notably between 10% and 50%, in particular between 15% and 40% by weight of lawsone relative to the total weight of the dry extract, the lawsone content being stable over time.

Preferably, after 1 month, 3 months, 6 months or 12 months at room temperature (15° C.-25° C.), with a relative humidity (RH) of 60%, and protected from light, the lawsone content of said extract that can be obtained by the method according to the invention does not decrease by more than 40%, preferably not more than 30%, in particular not more than 20%, notably not more than 15%, advantageously not more than 10%.

Advantageously, said extract contains at least 15%, preferably at least 20%, more advantageously at least 25% by weight of lawsone relative to the total weight of the dry extract; the percentages being expressed relative to the total weight of said dry extract (before any addition of a drying carrier).

Preferably, said extract according to the invention does not contain more than 2%, preferably not more than 1.5%, notably not more than 1% by weight of proteins, peptides or amino acids relative to the total weight of the dry extract.

Said extract also comprises chlorophylls, notably chlorophyll a and/or chlorophyll b, the total chlorophyll content being less than 25% by weight relative to the total weight of the dry extract, notably less than 20% by weight, advantageously less than 10% by weight relative to the weight of the dry extract.

Advantageously, said extract does not contain more than 5%, preferably not more than 2% by weight of chlorophylls relative to the total weight of the dry extract. Still more advantageously, said extract does not contain chlorophyll.

Said extract may also contain any compound naturally present in the aerial parts of *Lawsonia inermis*, notably the leaves and or branches of *Lawsonia inermis*. In particular, said extract also contains phenol compounds, such as gallic acid, para-coumaric acid, 2,3,4,6-tetrahydroxyacetophenone and 3,4,5-trihydroxyacetophenone; flavonoids, such as luteolin, apigenin, catechin, 3',4',5,7-tetrahydroxyflavanone, 3',5,7-trihydroxy-4'-methylflavone; sterols, such as β-sitosterol, triterpenes, such as lupeol; and/or heterosides thereof, such as lalioside, myrciaphenone A, 1,2-dihydroxy-4-O-glycosyloxynaphtalene (also called 4-O-β-D-glucopyranoside), luteolin-4'-O-glucoside, apigenin-7-O-β-glucoside, luteolin-3'-O-glucoside and apigenin-4'-O-β-glucoside.

In particular, said extract also contains phenol compounds, such as gallic acid, para-coumaric acid, 2,3,4,6-tetrahydroxyacetophenone and 3,4,5-trihydroxyacetophenone; flavonoids, such as luteolin, apigenin, catechin, 3',4', 5,7-tetrahydroxyflavanone, 3',5,7-trihydroxy-4'-methylflavone; and/or heterosides thereof, such as lalioside, myrciaphenone A, 1,2-dihydroxy-4-O-glycosyloxynaphtalene, luteolin-4'-O-glucoside, apigenin-7-O-β-glucoside, luteolin-3'-O-glucoside and apigenin-4'-O-β-glucoside.

More particularly, said extract also contains luteolin, apigenin and para-coumaric acid.

It may further contain 2,3,4,6-tetrahydroxyacetophenone, and optionally 3,4,5-trihydroxyacetophenone and 1,2-dihydroxy-4-O-glycosyloxynaphtalene.

In one embodiment, said extract may be standardized by the addition of a carrier, chosen from among protein-free carriers alone or in mixture.

The carrier can notably be chosen from among propanediol, pentanediol, glycerine, propylene glycol, methyl THF and amylic alcohol.

When said extract is a dry extract, the carrier is preferably chosen from among sugars and polysaccharide derivatives, such as fructose, glucose, sucrose, maltodextrins, cellulose derivatives, starch, notably maize, wheat or rice starch, agar-agar, gums, mucilages; and polyols such as mannitol, sorbitol, xylitol, etc.

In particular, it is selected from fructose, maltodextrins and starch, notably rice starch. It is preferably a natural carrier and/or of natural origin from renewable resources, as opposed to fossil resources, these carriers advantageously being obtainable by processes that respect the environment.

The present invention thus also relates to a standardized dry extract that can be obtained by the method mentioned above.

Such a standardized dry extract complies with the specifications defined previously.

In particular, said standardized dry extract contains between 0.6 and 1.4 wt. % of lawsone, and further contains luteolin, apigenin and para-coumaric acid.

More particularly, it is such that:
the luteolin content is comprised between 0.05 and 1.0 wt. %,
the apigenin content is comprised between 0.01 and 0.5 wt. %, and
the para-coumaric acid content is comprised between 0.01 and 0.5 wt. %.

It may further contain 2,3,4,6-tetrahydroxyacetophenone, and optionally 3,4,5-trihydroxyacetophenone and 1,2-dihydroxy-4-O-glycosyloxynaphtalene.

It may also contain any compound listed in Table 1.

Preferably, said standardized dry extract also complies with the specifications defined previously regarding the stability of the lawsone content over time.

Thus, after 1 month, 3 months, 6 months or 12 months at room temperature (15° C.-25° C.), with a relative humidity (RH) of 60%, and protected from light; or after 1 month, 3 months or 6 months at 40° C. (±2° C.), with a relative humidity (RH) of 75% (±5%), the lawsone content does not decrease by more 40%, preferably not more than 30%, in particular not more than 20%, notably not more than 15%, advantageously not more than 10%, more advantageously not more than 5%.

In one embodiment, the standardized dry extract that can be obtained by the method of the invention contains at least 80%, advantageously at least 90%, notably at least 92%, in particular at least 95% by weight of carrier, relative to the total weight of the standardized dry extract.

In the rest of the description, "extract according to the invention" will designate the extract as such, as defined above, or the extract that can be obtained by the method according to the invention such as described above.

Likewise, "standardized dry extract according to the invention" will designate the standardized dry extract as such, as defined above, or the standardized dry extract that can be obtained by the method according to the invention such as described above.

The invention also relates to a composition comprising an extract or a standardized dry extract according to the invention, and, if applicable, an appropriate excipient. The extract and the standardized dry extract according to the invention are such as defined in the paragraphs above concerning the extract and the standardized dry extract as such and those concerning the extract and the standardized dry extract that can be obtained by the method according to the invention.

Hence, said extract and standardized dry extract contain luteolin, apigenin and para-coumaric acid, and may further contain 2,3,4,6-tetrahydroxyacetophenone, and optionally 3,4,5-trihydroxyacetophenone and 1,2-dihydroxy-4-O-glycosyloxynaphtalene.

In particular, the standardized dry extract has a lawsone content comprised between 0.6% and 1.4%, in particular, approximately 1.3% by weight of lawsone relative to the total weight of the extract.

Said composition is preferably formulated to be administered externally and topically.

The composition according to the invention may be formulated in the form of different preparations suited to topical administration and notably including creams, emulsions, milks, ointments, lotions, oils, aqueous or water-alcohol or glycolic solutions, powders, sprays, shampoos, varnishes or any other product for external application.

The composition is advantageously a cosmetic dye composition, comprising at least one cosmetically-acceptable excipient.

"Cosmetically-acceptable excipient" means, in the context of the present invention, one that is useful in the preparation of a cosmetic composition, which is generally safe, non-toxic and neither biologically nor otherwise undesirable and which is acceptable for a cosmetic use, notably by topical application.

Notably, the composition according to the present invention may also comprise at least one cosmetically-acceptable excipient known to the skilled person, chosen from among surfactants, thickeners, preservatives, fragrances, dyes, chemical or mineral filters, moisturizers, thermal waters, etc. The skilled person knows to adjust the formulation of the composition according to the invention by using their general knowledge.

However, the composition is free of the stabilizers usually present in henna compositions to stabilize lawsone.

Thus, the cosmetic dye composition according to the invention is free of additives made of synthetic dyes, such as diaminotoluenes and diaminobenzenes, especially PPD (para-diphenylenediamine) which is most often used, or heavy metals [Wang et al. *J. environ. Anal. Toxicol.* 2016, 6(3); Wang et al. *J. Chromatogr. B* 2011, 879, 1795-1801].

In one particular embodiment, the cosmetic dye composition according to the invention comprises 0.01 to 50%, notably 1 to 40%, in particular 2 to 30% by weight of the extract according to the invention, the weight of the extract being expressed in dry extract relative to the total weight of the composition.

In one particular embodiment, the cosmetic dye composition according to the invention comprises 1 to 20%, notably 5 to 20%, in particular 10 to 20% by weight of the standardized extract according to the invention, the weight of the standardized extract being expressed in dry extract relative to the total weight of the composition.

Preferably, the cosmetic dye composition according to the invention has a lawsone content comprised between 0.2% and 2%, notably between 0.5 and 1.5% by weight of lawsone relative to the total weight of the composition.

In particular, the cosmetic dye composition has a lawsone content of approximately 1.3% by weight with regard to the total weight of the composition.

This lawsone content may be obtained by the addition of a carrier, chosen from among protein-free carriers alone or in mixture.

The carrier can notably be chosen from among propanediol, pentanediol, glycerine, propylene glycol, methyl THF and amylic alcohol.

When the cosmetic dye composition according to the invention is in powder form, the carrier is preferably chosen from among sugars and polysaccharide derivatives, such as fructose, glucose, sucrose, maltodextrins, cellulose derivatives, starch, notably maize, wheat or rice starch, agar-agar, gums, mucilages; and polyols such as mannitol, sorbitol, xylitol, etc.

When the cosmetic dye composition according to the invention is in powder form, the skilled person can adjust its particle size by any method well known to them.

In particular, a cosmetic dye composition according to the invention may be in the form of powder, with a particle size less than 250 µm.

Preferably, a cosmetic dye composition according to the invention does not contain more than 2% by weight of proteins, peptides or amino acids relative to the total weight of the dry extract.

The cosmetic dye composition according to the invention may also comprise one or more additional dye(s) and/or pigment(s).

It is understood that, preferably, the lawsone content of a composition according to the invention is stable over time.

Thus, after 1 month, 3 months, 6 months or 12 months at room temperature (15° C.-25° C.), with a relative humidity (RH) of 60%, and protected from light, the lawsone content of said extract does not decrease by more than 60%, notably not more than 50%, preferably not more than 50%, more preferably not more than 30%, in particular not more than 20%, notably not more than 15%, advantageously not more than 10%.

The present invention also concerns a cosmetic method for dying keratin fibers comprising the application of a composition according to the invention onto keratin fibers, optionally followed by rinsing.

"Keratin fibers" means the keratin present in the epidermis and integuments, such as hair and nails.

The present invention also concerns a method for tattooing the skin.

The present invention also has for a subject a textile or furniture dye comprising an extract according to the invention.

Such a dye may also comprise one or more additional dye (s) and/or pigment(s).

The dye according to the present invention may also comprise any adjuvant known to the skilled person, who knows how to adjust the formulation of the dye according to the invention by using their general knowledge.

The present invention also relates to a use of such a dye for dying textile or wood fibers.

FIGURES

FIG. 1 represents the UHPLC-UV chromatogram of an extract according to the invention (sample E2) (ACQUITY UPLC BEH Shield RP18 column (100 mm×2.1, 1.7 µm) equipped with a Vanguard™ precolumn (5 mm×2.1) (Waters Corporation, Milford, USA) at 35° C.; flow rate: 0.4 mL/min; mobile phase: linear gradient system of (A) water with 0.1% formic acid and (B) acetonitrile and (C) methanol (wash solvent): 0-9 min, 2%-100% B; 9-9.55 min, maintain 100% B; 9.55-9.70 min, 0%-100% C; 9.7-10.2 min, maintain 100% C; 10.20-10.35 min, 0%-100% B; 10.35-10.85 min, maintain 100% B; 10.85-11 min, 0%-98% A; held at 98% A-2% B for 1 min for equilibration of the column.

EXAMPLES

Figure 1:
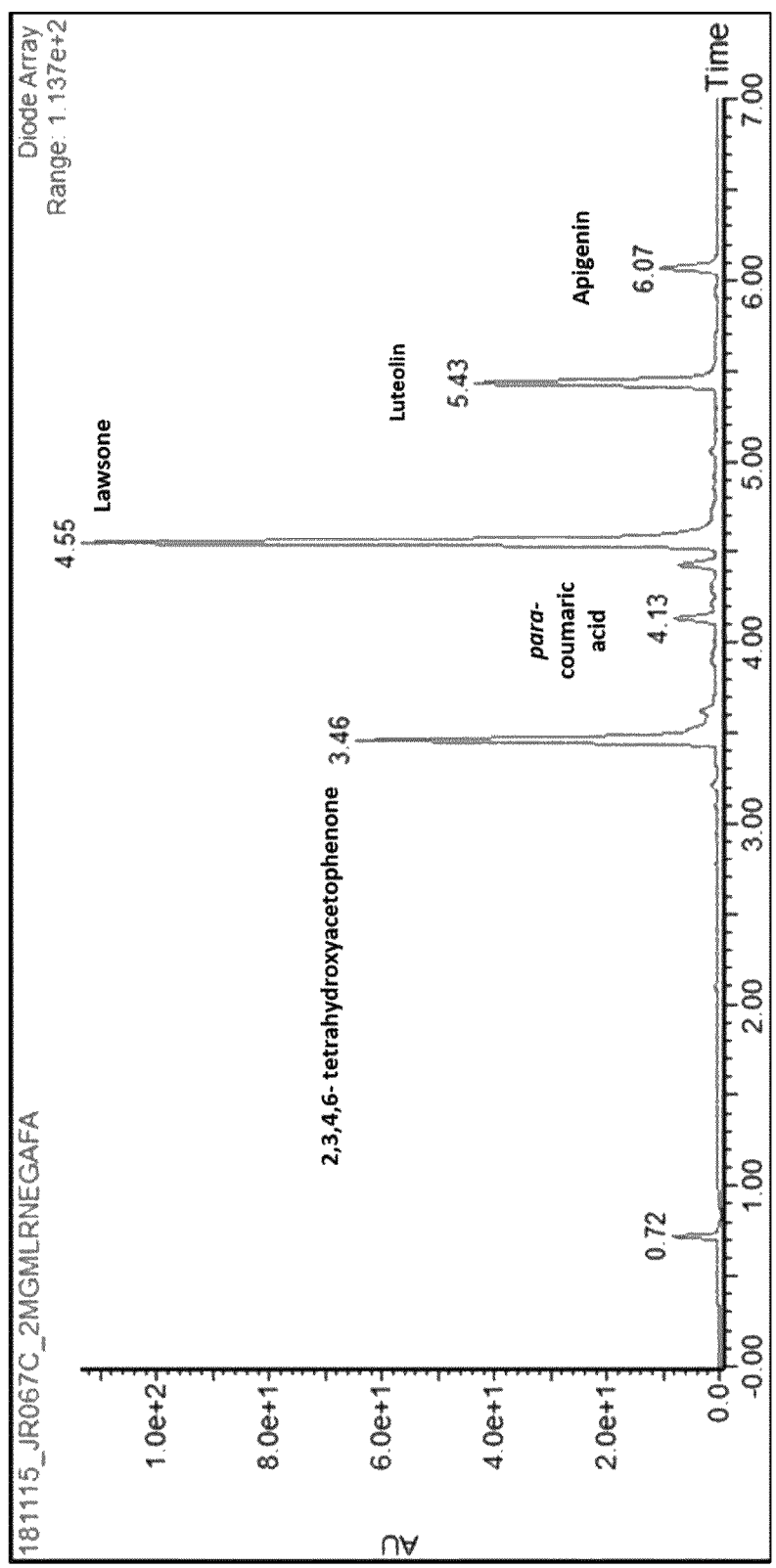

The examples that follow illustrate the invention.
I. Extract, Standardized Dry Extract and Preparation Method of the Invention Example 1: Isopropyl Acetate Extract No 1 According to the Invention 50 g of uncrushed leaves of *Lawsonia inermis* are extracted by 500 mL of water at 30-40° C. for 30 min. 600 mL of isopropyl acetate are added to this solution. This is mixed for 30 min. After decantation, the upper isopropyl acetate phase (480 mL) is recovered, the aqueous phase being separated because it is practically free of lawsone. The isopropyl acetate phase is filtered then dried with the Rotavapor. The residue is the dry henna extract (sample E1).

The plant contains 1.5 g of lawsone/100 g of dry plant. The isopropyl acetate phase contains 80.7% of the lawsone potential present in the plant.

The dry henna extract (sample E1) contains 30.2% of lawsone, i.e. 71% of the lawsone present in the plant.

Stability study: sample stored at 25° C., 60% relative humidity and protected from light:
At T0: lawsone content=30.2% by weight of lawsone relative to the weight of the dry extract.
At T1 month: lawsone content=29.7% by weight of lawsone relative to the weight of the dry extract; namely no significant loss within the meaning of the present invention.

Example 2: Isopropyl Acetate Extract No 2 According to the Invention 49.5 g of uncrushed leaves of *Lawsonia inermis* are extracted by 500 mL of water at 30-40° C. for 30 min. 600 mL of isopropyl acetate are added to this solution. This is mixed for 30 min. After decantation, the upper isopropyl acetate phase is recovered and filtered on Buchner (K900), and the residue is rinsed with 50 mL of isopropyl acetate. The resulting solution is then dried with the Rotavapor. The residue is the dry henna extract (sample E2).

The dry henna extract (sample E2) contains 30.9 wt. % of lawsone.

Example 3: Ethyl Acetate Standardized Dry Extract According to the Invention 50 g of crushed leaves of *Lawsonia inermis* are extracted by 500 mL of water at 30-40° C. for 30 min. 600 mL of ethyl acetate are added to this solution. This is mixed for 30 min. After decantation, the upper ethyl acetate phase is recovered and the aqueous phase is removed because of its very low lawsone content.

The lawsone content of the ethyl acetate phase is determined by H.P.L.C, and maltodextrin is added in sufficient quantity to obtain a mixture containing 1.3 wt % of lawsone, which is then lyophilized.

The dry henna extract standardized with maltodextrin (sample E3) contains 1.1 wt. % of lawsone, i.e. 71% of the initial lawsone content in the plant.

For comparative purposes, counter-examples are described hereinafter.

Counter-Example 1: Acidic Isopropyl Acetate Extract No 1

20 g of uncrushed *Lawsonia inermis* leaves are extracted by 60 mL of isopropyl acetate saturated by phosphoric acid (1N $H_3PO_4$) at room temperature for 60 min. After solid/liquid separation on Buchner (K900) and rinsing of the residue by 20 mL of isopropyl acetate saturated in 1N $H_3PO_4$, the liquids obtained are collected and assayed (sample CE1)

The plant contains 1.52 g of lawsone/100 g of dry plant. Sample CE1 contains 0.9% of the lawsone potential present in the plant.

Counter-Example 2: Acidic Methyl Ethyl Ketone Extract 20 g of uncrushed *Lawsonia inermis* leaves are extracted by 60 mL of methyl ethyl ketone saturated by phosphoric acid (1N $H_3PO_4$) at room temperature for 60 min. After solid/liquid separation in Buchner funnel (K900) and rinsing of the residue by 20 mL of methyl ethyl ketone saturated in 1N $H_3PO_4$, the liquids obtained are collected and assayed (sample CE2).

The plant contains 1.52 g of lawsone/100 g of dry plant. Sample CE2 contains 0.9% of the lawsone potential present in the plant.

Counter-Example 3: Limewater Extract No 1

20 g of uncrushed *Lawsonia inermis* leaves are extracted by 80 mL of limewater at room temperature for 60 min. After solid/liquid separation in Buchner funnel (K900) and rinsing of the residue by 20 mL of limewater, the liquids obtained are collected and assayed (sample CE3).

The plant contains 1.52 g of lawsone/100 g of dry plant. Sample CE3 contains 24% of the lawsone potential present in the plant.

Counter-Example 4: Limewater Extract No 2

19.75 g of crushed *Lawsonia inermis* leaves are extracted by a mixture of 80 mL of water and 20 mL of limewater (CaO(OH)$_2$, 50 g/L) at room temperature for 60 min. After solid/liquid separation in Buchner funnel (K900) and rinsing of the residue by 50 mL of water, the liquids obtained are collected and then dried with the Rotavapor. The residue is the dry henna extract (sample CE4).

The dry henna extract (sample CE4) contains 1.8 wt. % of lawsone.

Counter-Example 5: Acidic Isopropyl Acetate Extract No 2

20.0 g of crushed *Lawsonia inermis* leaves are extracted by 60 mL of isopropyl acetate saturated by phosphoric acid (1N H$_3$PO$_4$) at room temperature for 60 min. After solid/liquid separation in Buchner funnel (K900) and rinsing of the residue by 20 mL of saturated isopropyl acetate, the liquids obtained are collected and then dried with the Rotavapor. The residue is the dry henna extract (sample CE5).

The dry henna extract (sample CE5) contains 0.2 wt. % of lawsone.

Counter-Example 6: Aqueous Solution Extract 50 g of uncrushed *Lawsonia inermis* leaves are extracted by 150 mL of an acid aqueous solution (HCl, pH=2.5) at room temperature for 30 min. The mash obtained is separated into a pomace and an aqueous solution on Buchner without filter. The pomace is extracted with 1 L of an alkaline aqueous solution (NaOH 0.15%) at 50° C. for 3 h. After solid/liquid separation by filtration (on a gauze of size 100 mesh), the obtained solution is concentrated under vacuum to 1/15, cooled and acidified with HCl to pH=2.5. It is then centrifuged and oven-dried under vacuum at 40° C. The residue is the dry henna extract (sample CE6).

The dry henna extract (sample CE6) contains 9.5 wt. % of lawsone.

For ease of comparison, significant aspects of extracts E2, CE4, CE5 and CE6 are summarized below. Of note, the comparison of said extracts is of particular relevance, given that the same plant lot was used as starting material.

|  | E2 | CE4 | CE5 | CE6 |
|---|---|---|---|---|
| Starting plant material (g) | 49.5 | 19.75 | 20.0 | 50.0 |
| Lawsone content in the starting material (mg) | 896 | 357 | 362 | 905 |
| Extracted quantity of lawsone (mg) | 580 | 41 | 0.48 | 213 |
| Lawsone yield (Lawsone potential of the plant) | 64.7% | 11.5% | 0.1% | 23.5% |
| Lawsone content in the dry extract | 30.9% | 1.8% | 0.2% | 9.5% |

As it appears clearly from the results displayed in the table above, the method of the invention allows to extract a much more important part of the lawsone potential of the plant than other methods. This is notably due to the specific maceration step a), during which the glycosylated lawsone derivatives originally present in the plant undergo an enzymatic hydrolysis.

II. Characterization Studies

A) Structural Analyses
Material and Methods

The extract of the invention that was used for analyses is sample E2.

Chromatographic separations were performed on a Waters ACQUITY UHPLC system equipped with a quaternary pump, an auto-sample injector, an on-line degasser, an automatic thermostatic column oven and a DAD detector (200-500 nm). An ACQUITY UPLC BEH Shield RP18 column (100 mm×2.1, 1.7 μm) equipped with a Vanguard™ precolumn (5 mm×2.1) (Waters Corporation, Milford, USA) at 35° C. was used and the flow rate was set at 0.4 mL/min. The mobile phase consisted of a linear gradient system of (A) water with 0.1% formic acid and (B) acetonitrile and (C) methanol as wash solvent: 0-9 min, 2%-100% B; 9-9.55 min, maintain 100% B; 9.55-9.70 min, 0%-100% C; 9.7-10.2 min, maintain 100% C; 10.20-10.35 min, 0%-100% B; 10.35-10.85 min, maintain 100% B; 10.85-11 min, 0%-98% A; held at 98% A-2% B for 1 min for equilibration of the column.

Compounds were identified by high-resolution mass spectrometry, 1D- and 2D-NMR experiments ($^1$H NMR, $^{13}$C NMR, DEPT, COSY, HMBC, HSQC).

NMR experiments were performed on a Bruker Avance IIIHD 500 MHz spectrometer equipped with a BBO Prodigy 5 mm probe (Bruker Biospin, Karlsruhe, Baden-Wûttemberg, Germany). Deuterated. dimethylsulfoxide was used as solvent. Acquisition sequences were $^1$H, $^{13}$C, COSY, HSQC, HMBC. Chemical shifts were adjusted with the solvent as an internal standard ($\delta_H$ 2,52 ppm and $\delta_C$ 39,52 ppm).

HRMS data were obtained on a Synapt G2Si with Masslynx v4.1 SCN957 software (Waters Q-TOF SYNAPT™, Waters Corp, Manchester, England). The MS source temperature was set at 125° C. and the desolvation temperature was set at 500° C. Nitrogen was used as the dry gas: the desolvation gas flow rate was set at 1000 L/h; the cone gas flow was maintained at 50 L/h. In both positive and negative modes, capillary and cone voltages were set at 0.5 kV and 50 V respectively. The mass spectra were recorded across the range of 100-1500 Da. To ensure stable and precise scanning, leucine enkephalin was used as reference compound (positive ion mode ([M+H]+=556.2771 and 278.1141) and negative ion mode ([M−H]−=554.2615 and 236.1035)).). All data were acquired in continuum mode with a resolving power of 25,000.

Results

UHPLC-UV Chromatogram

Figure 2:
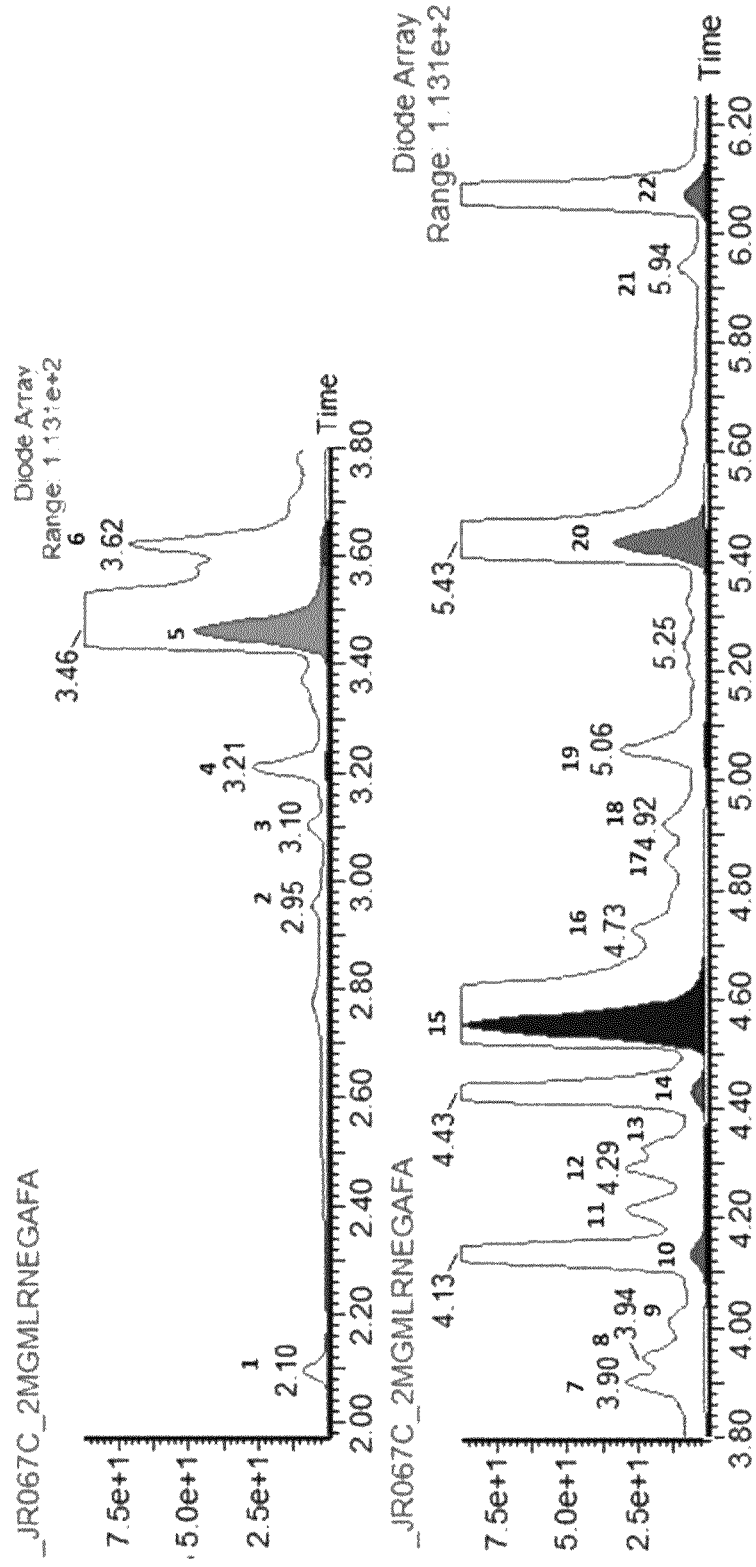
FIG. 2 represents the same chromatogram as in FIG. 1: the filled peaks correspond to the ones that can be seen in FIG. 1, while the plain line corresponds to a zoom of said chromatogram.
Figure 3A:
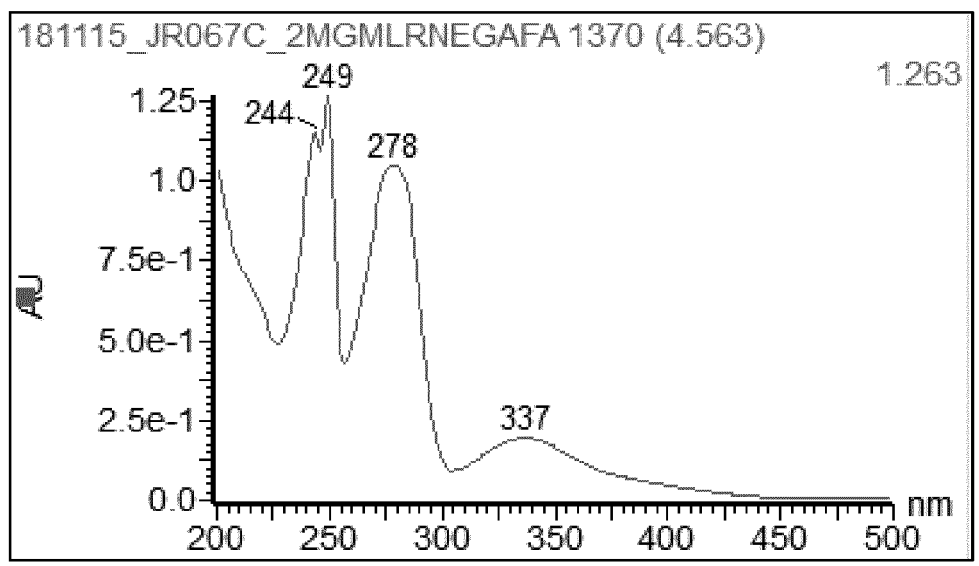
FIGS. 3a, 3b, 3c, 3d and 3e represent the UV spectra of lawson, luteolin, apigenin, para-coumaric acid and 2,3,4,6-tetrahydroxyacetophenone, isolated from sample E2.
Figure 3B:
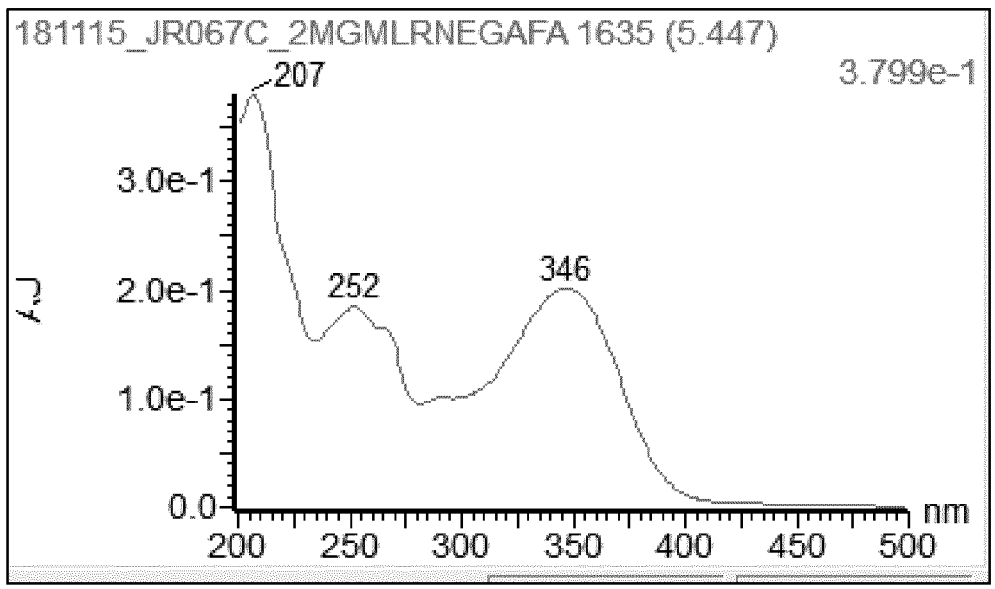
Figure 3C:
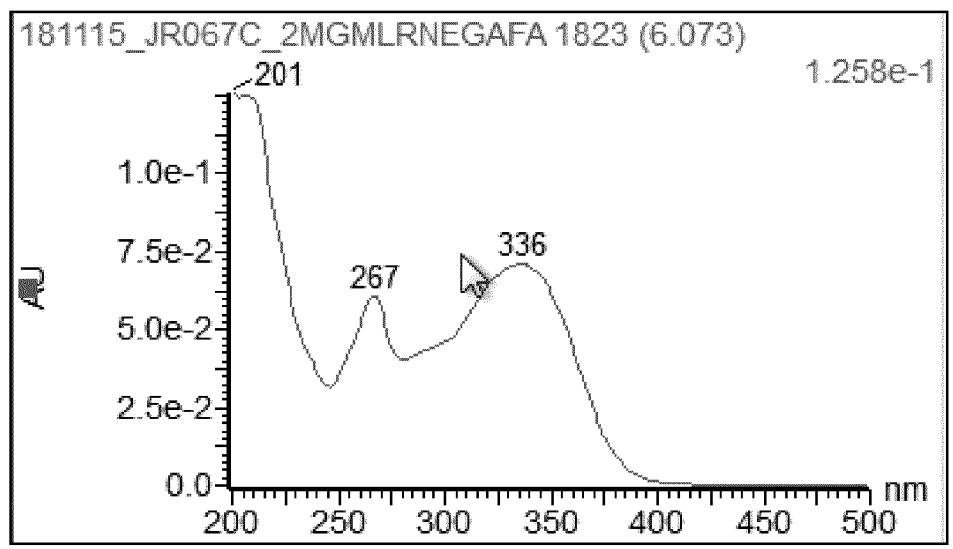
Figure 3D:
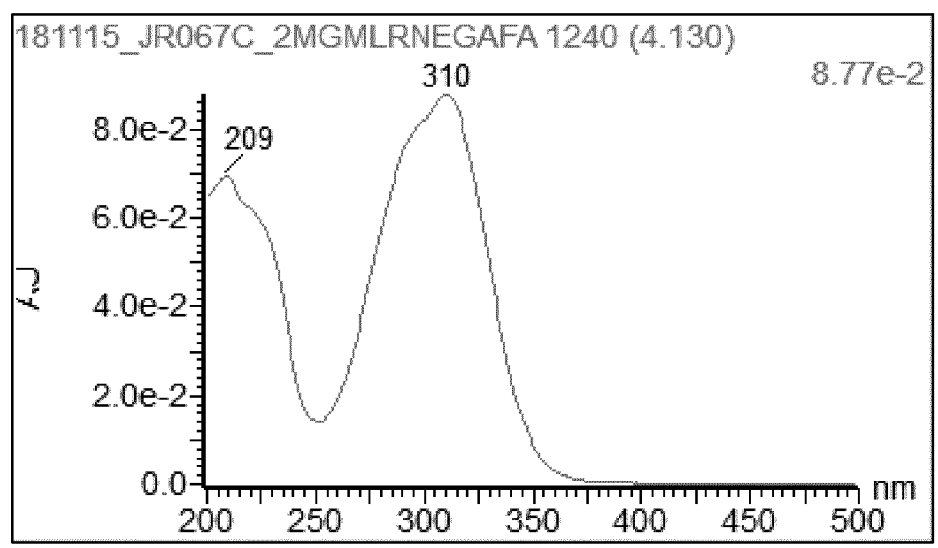
Figure 3E:
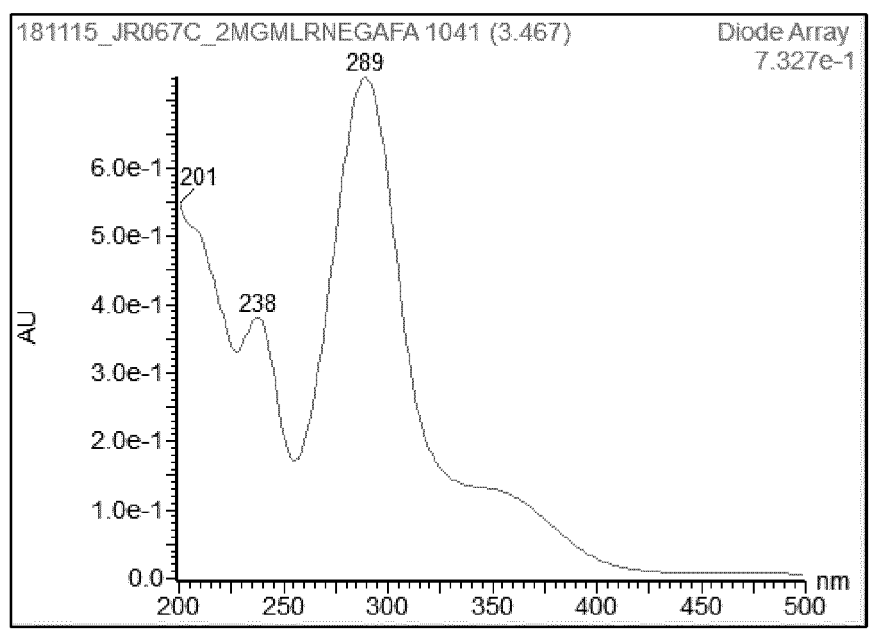
Figure 4A:
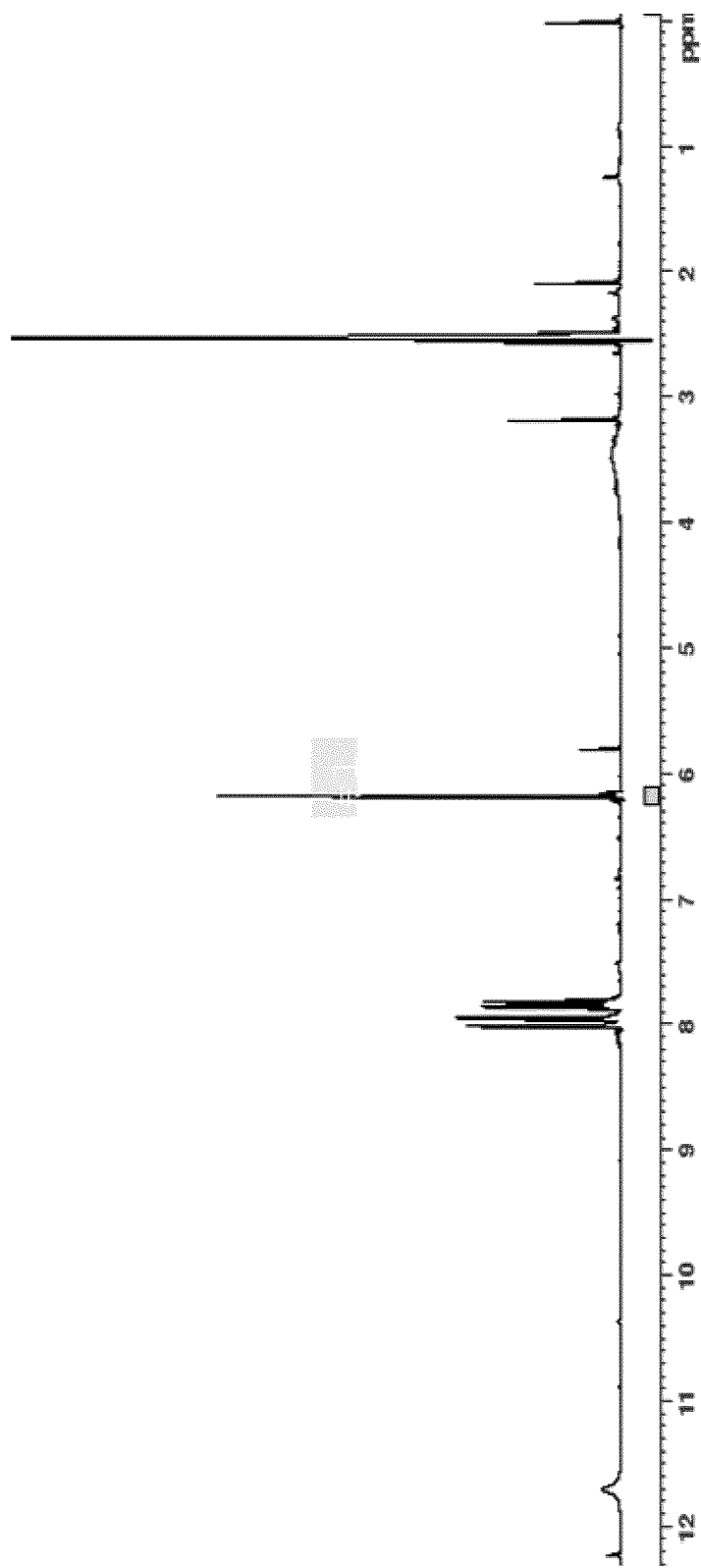
FIGS. 4a, 4b, 4c, 4d and 4e represent the $^1$H, $^{13}$C, COSY, HSQC and HMBC NMR spectra of lawson isolated from sample E2.
Figure 4B:
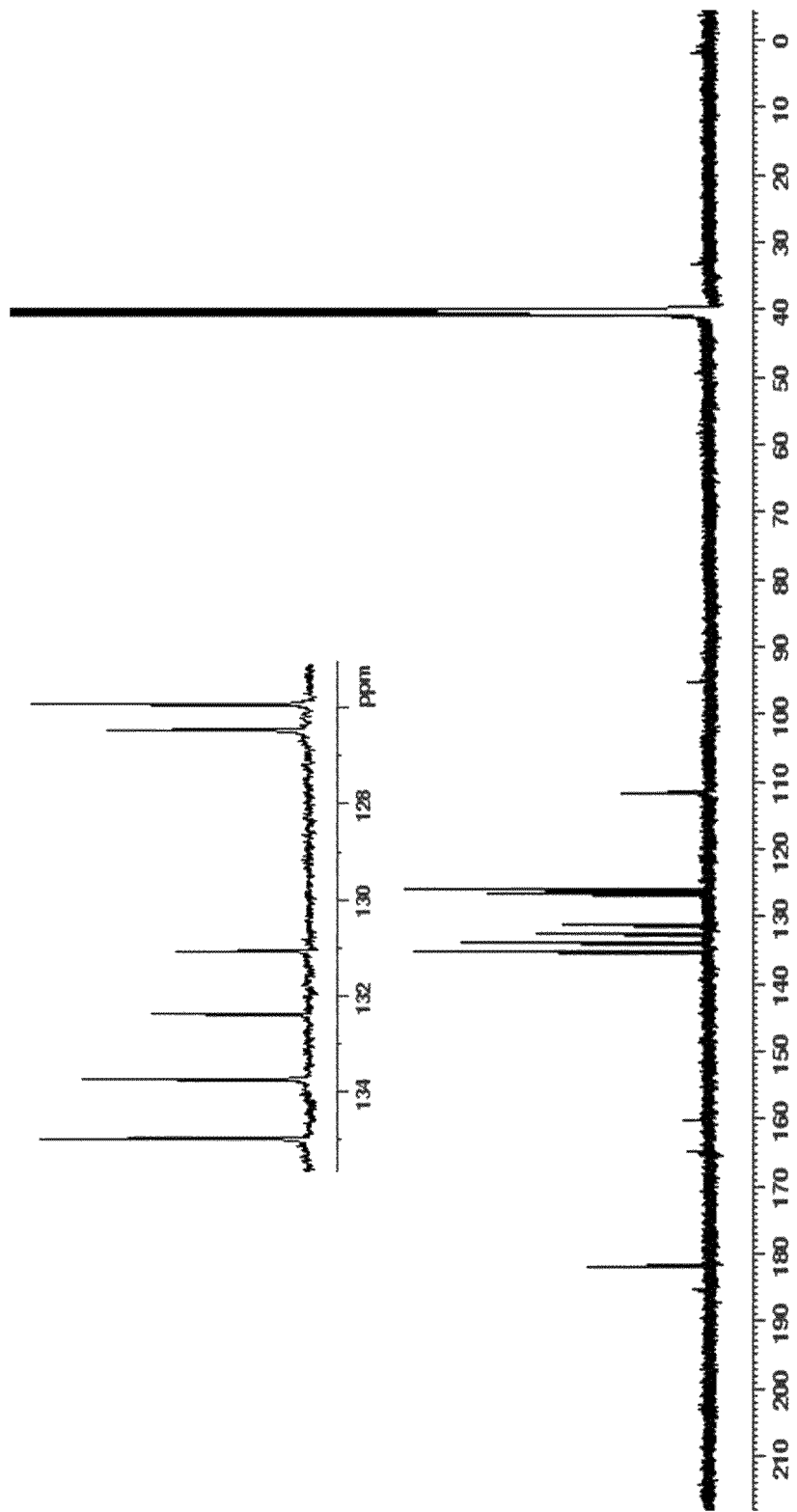
Figure 4C:
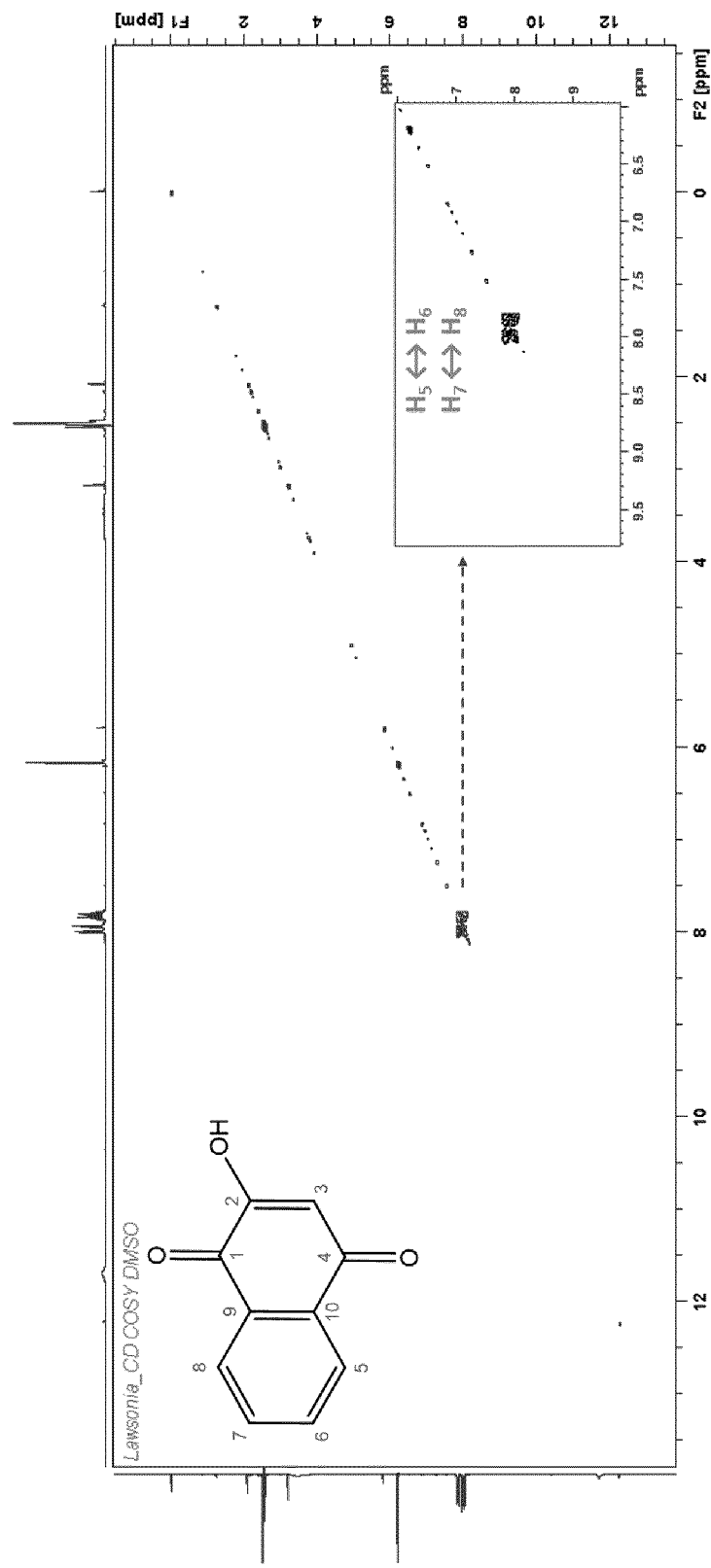
Figure 4D:
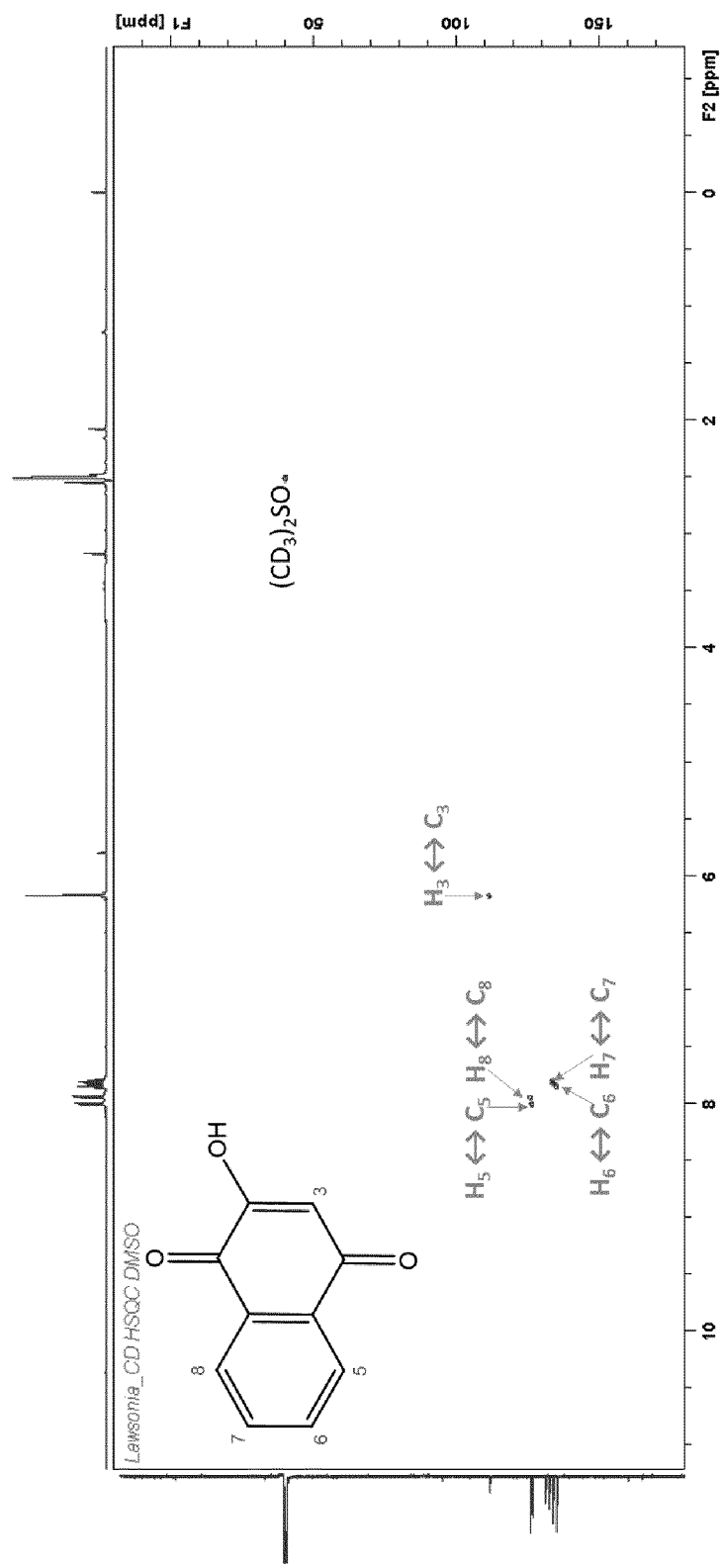
Figure 4E:
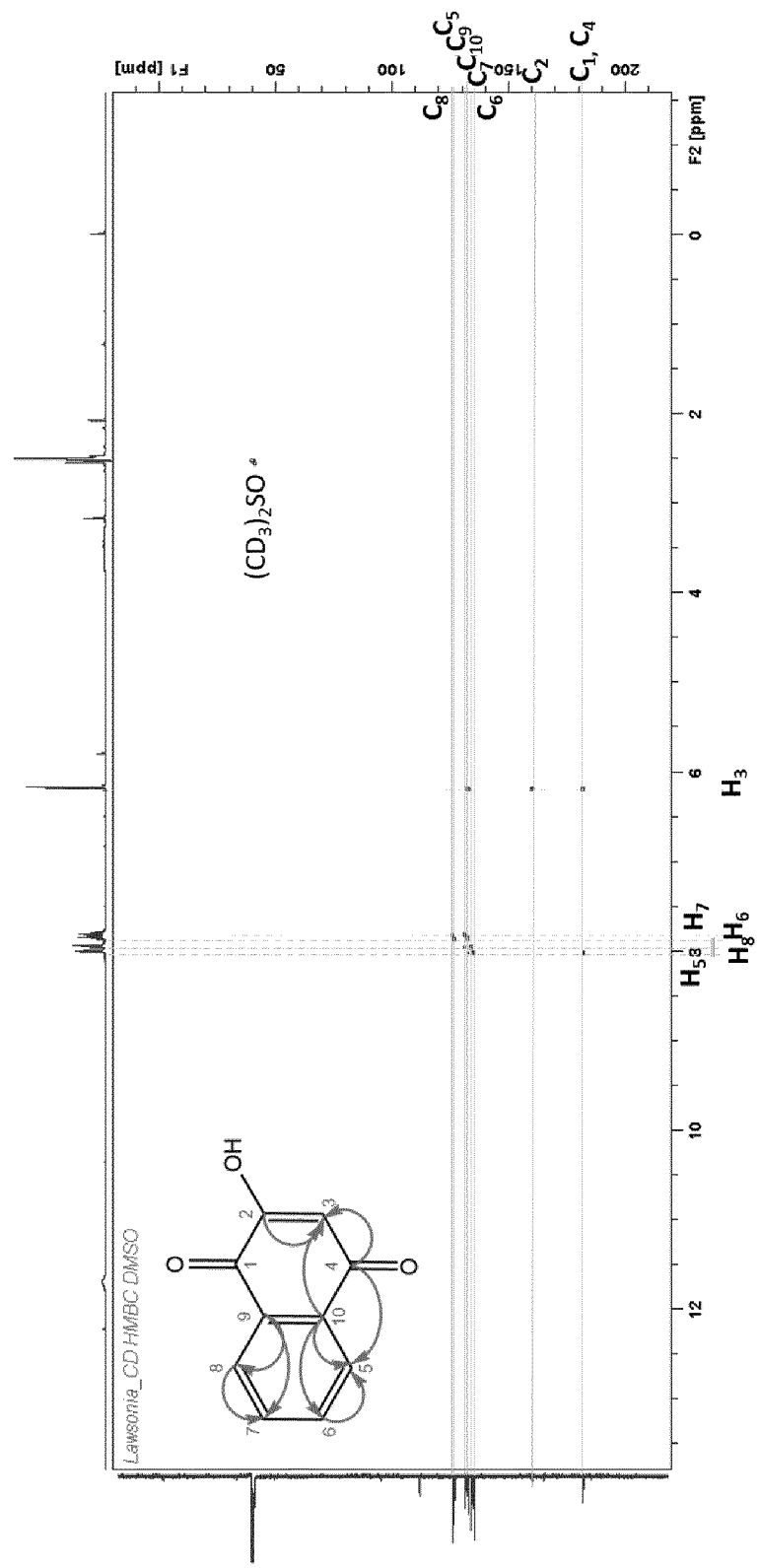
Figure 5A:
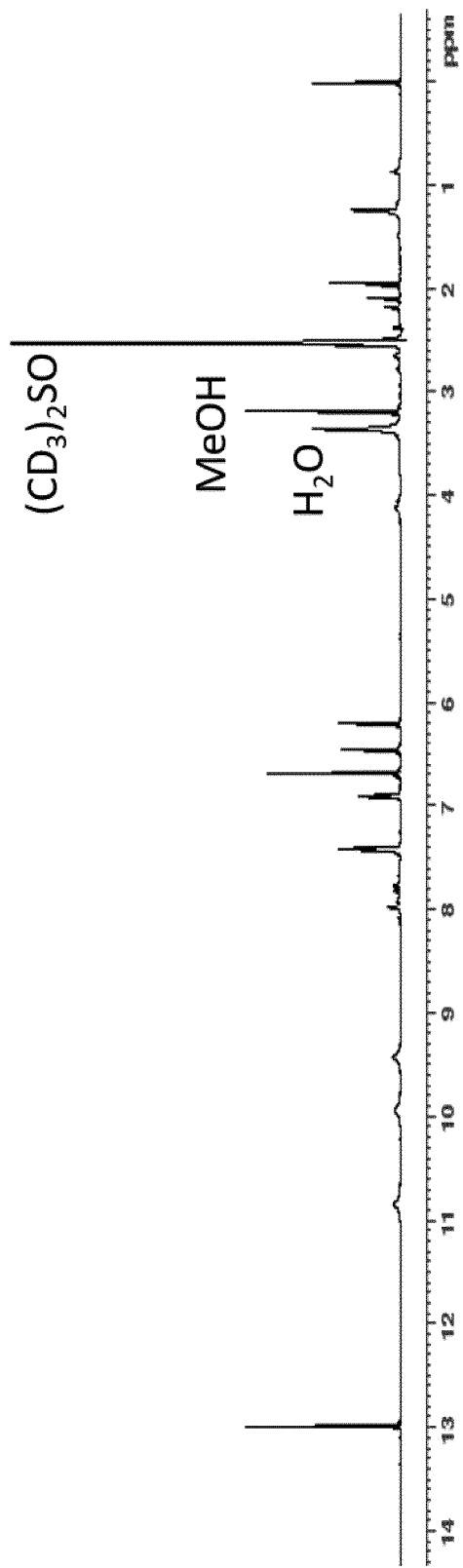
FIGS. 5a, 5b, 5c, 5d and 5e represent the $^1$H, $^{13}$C, COSY, HSQC and HMBC NMR spectra of luteolin, isolated from sample E2.
Figure 5B:
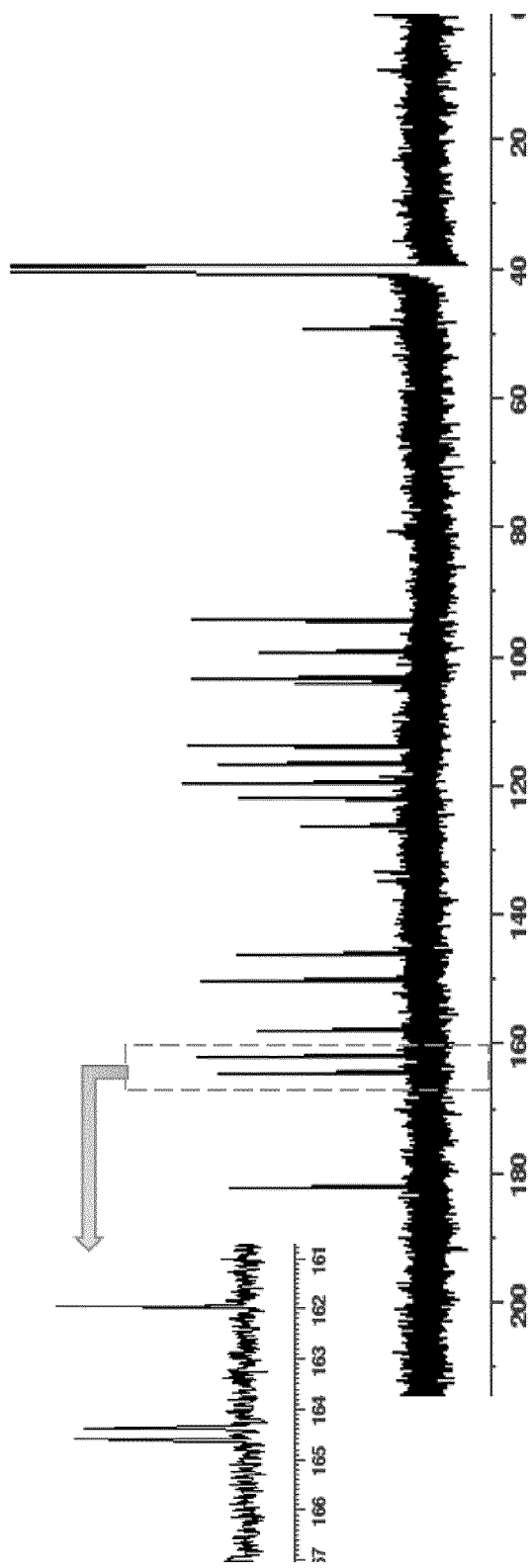
Figure 5C:
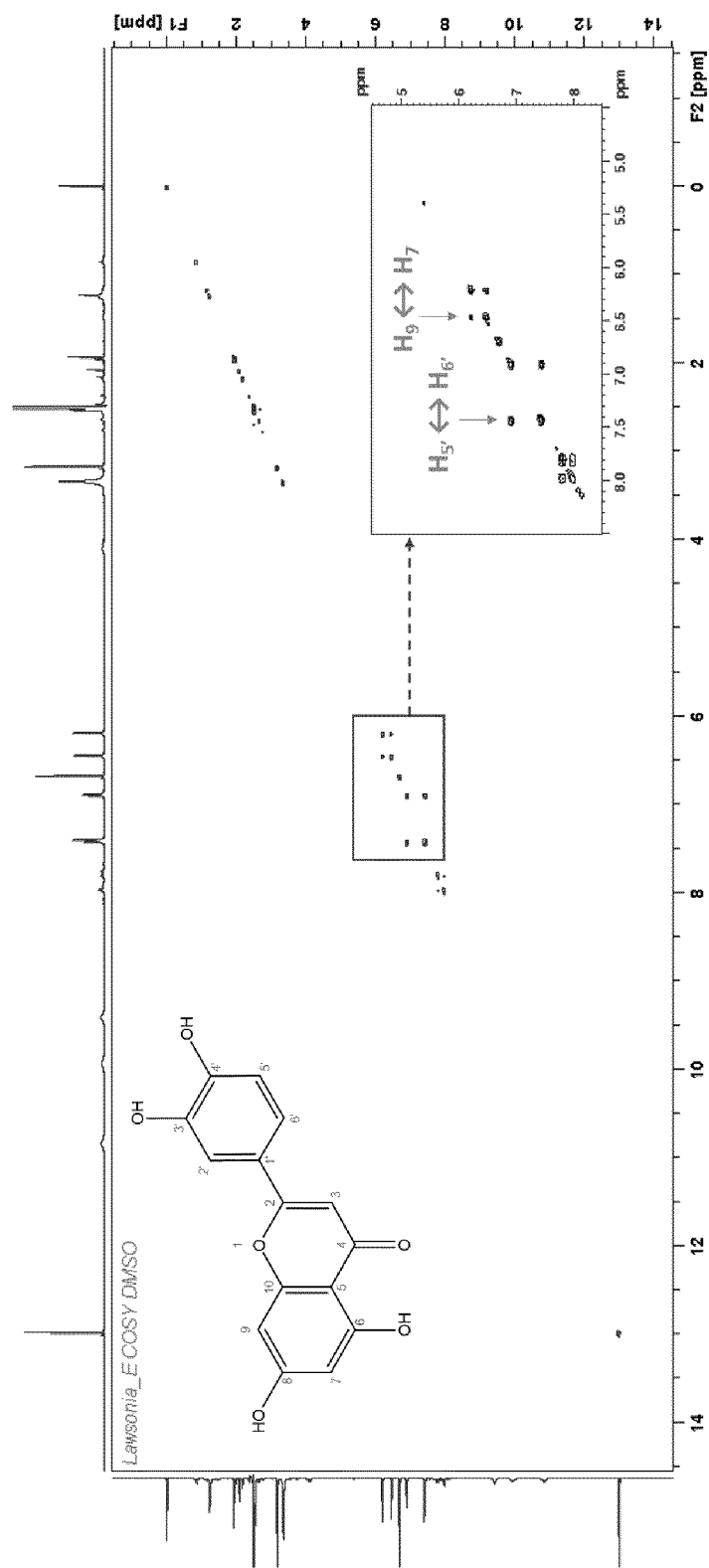
Figure 5D:
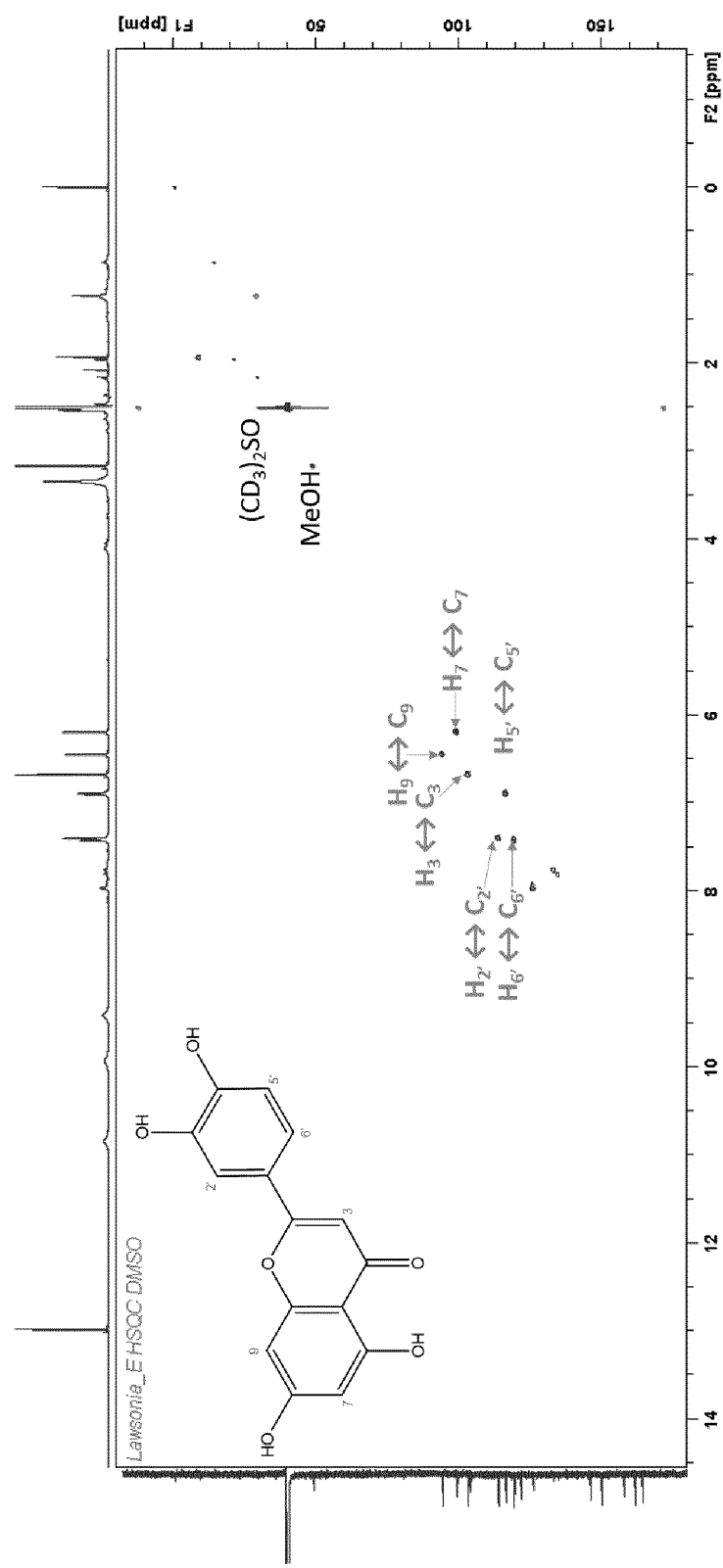
Figure 5E:
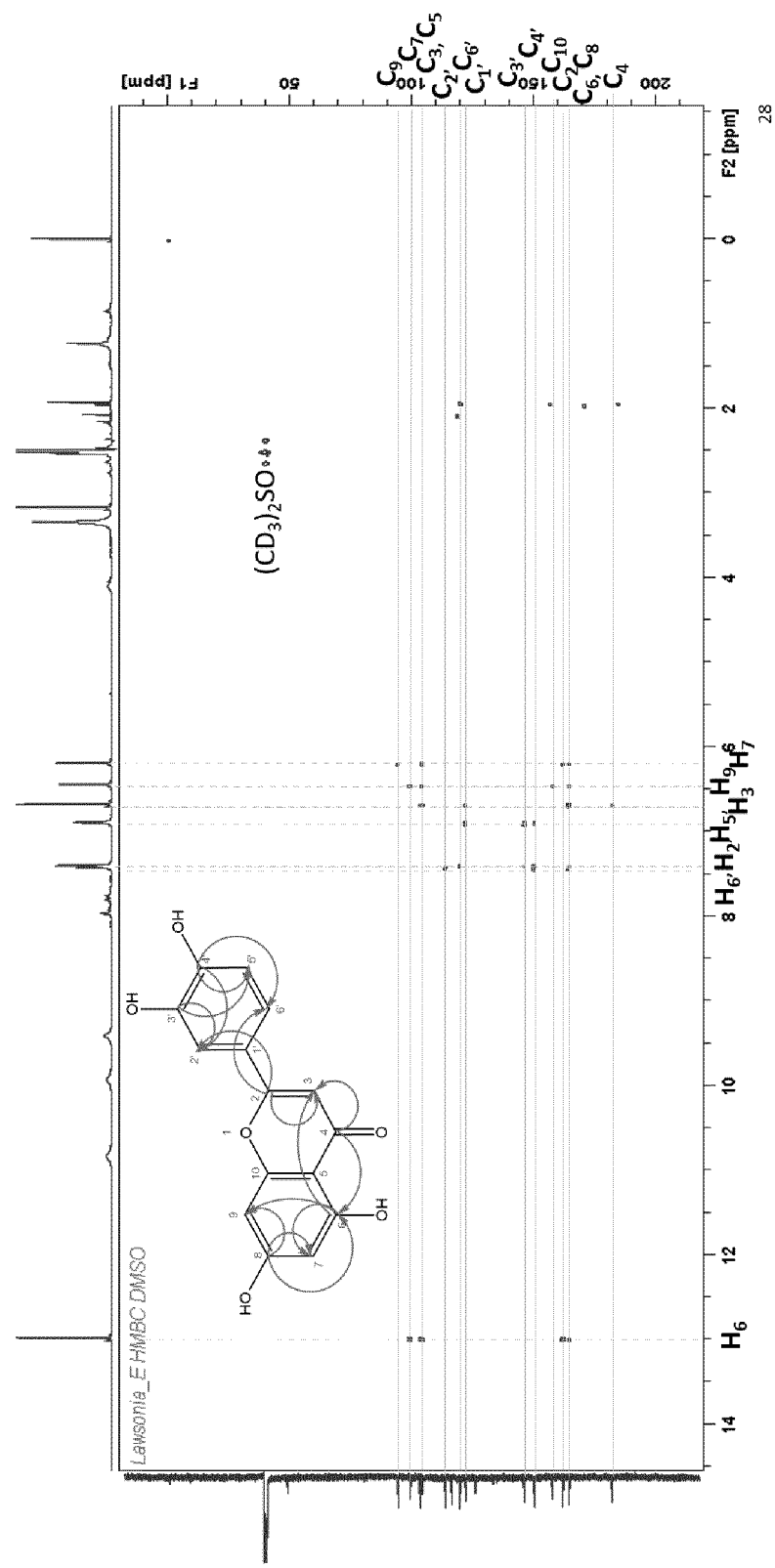
Figure 6A:
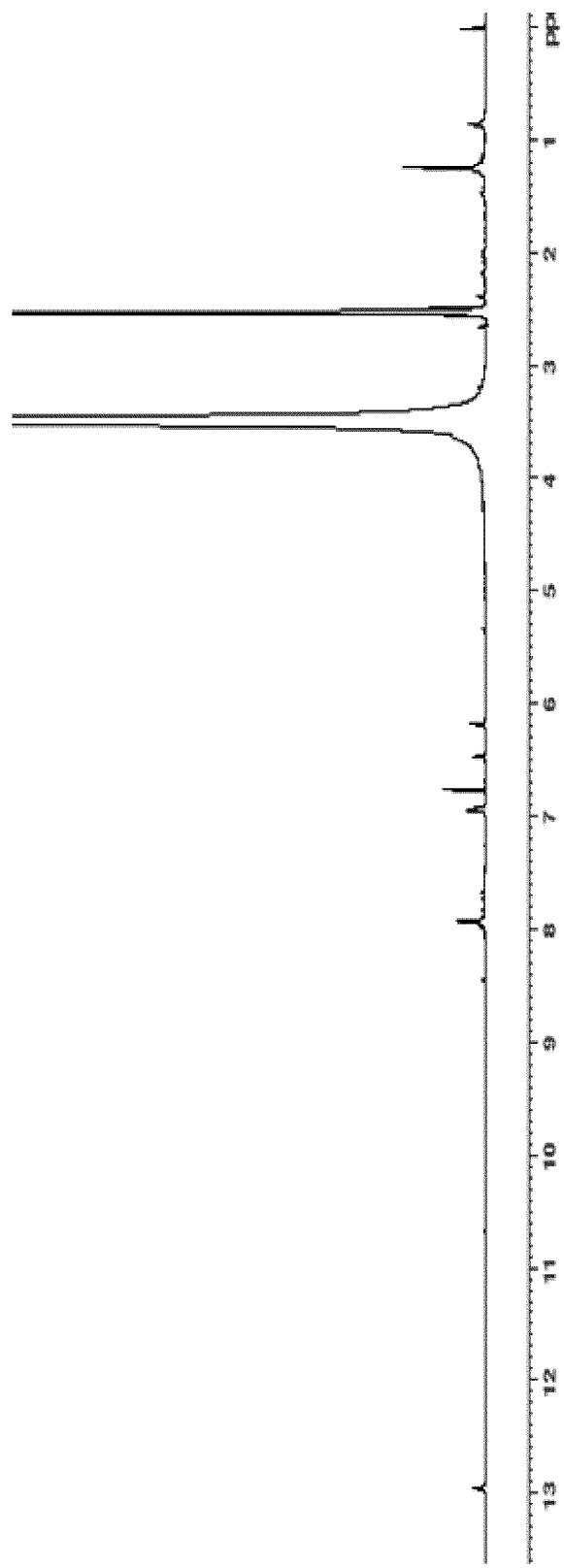
FIGS. 6a, 6b, 6c, 6d and 6e represent the $^1$H, $^{13}$C, COSY, HSQC and HMBC NMR spectra of apigenin, isolated from sample E2.
Figure 6B:
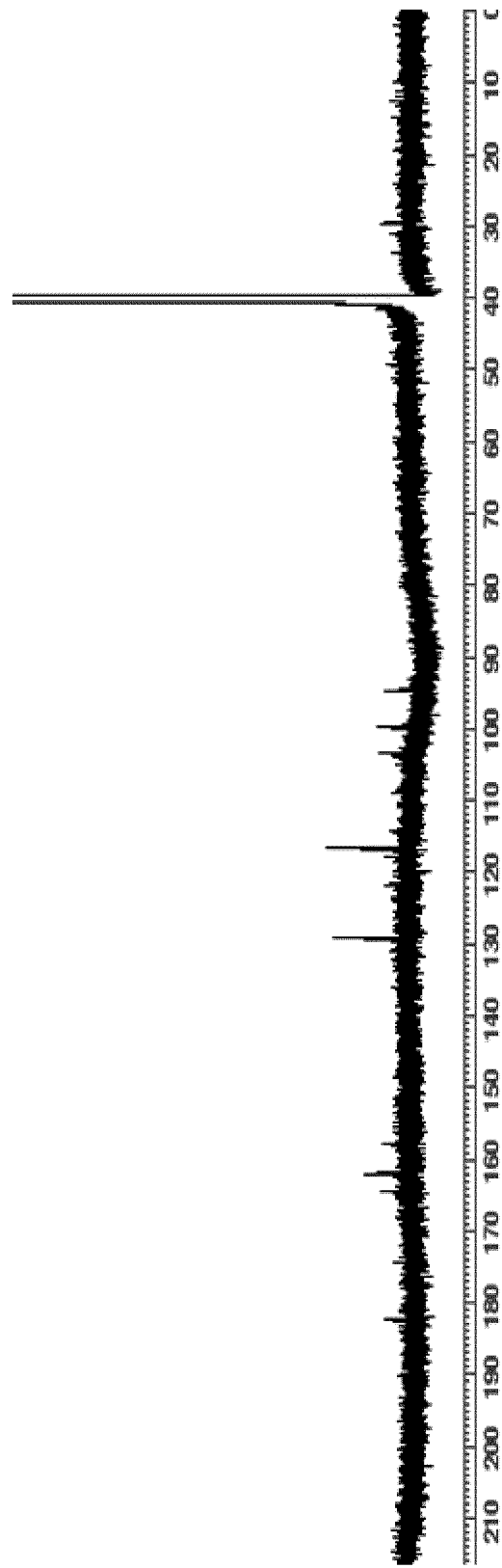
Figure 6C:
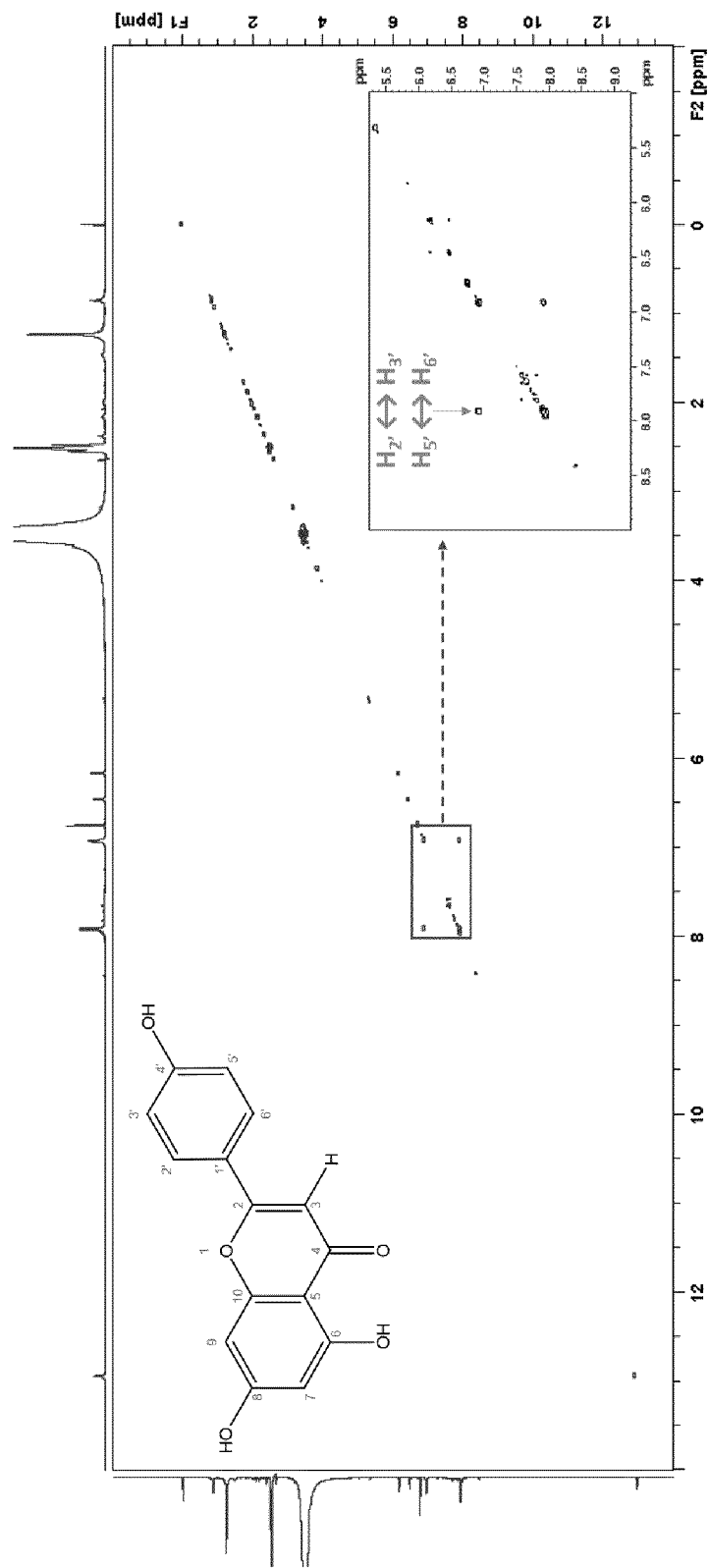
Figure 6D:
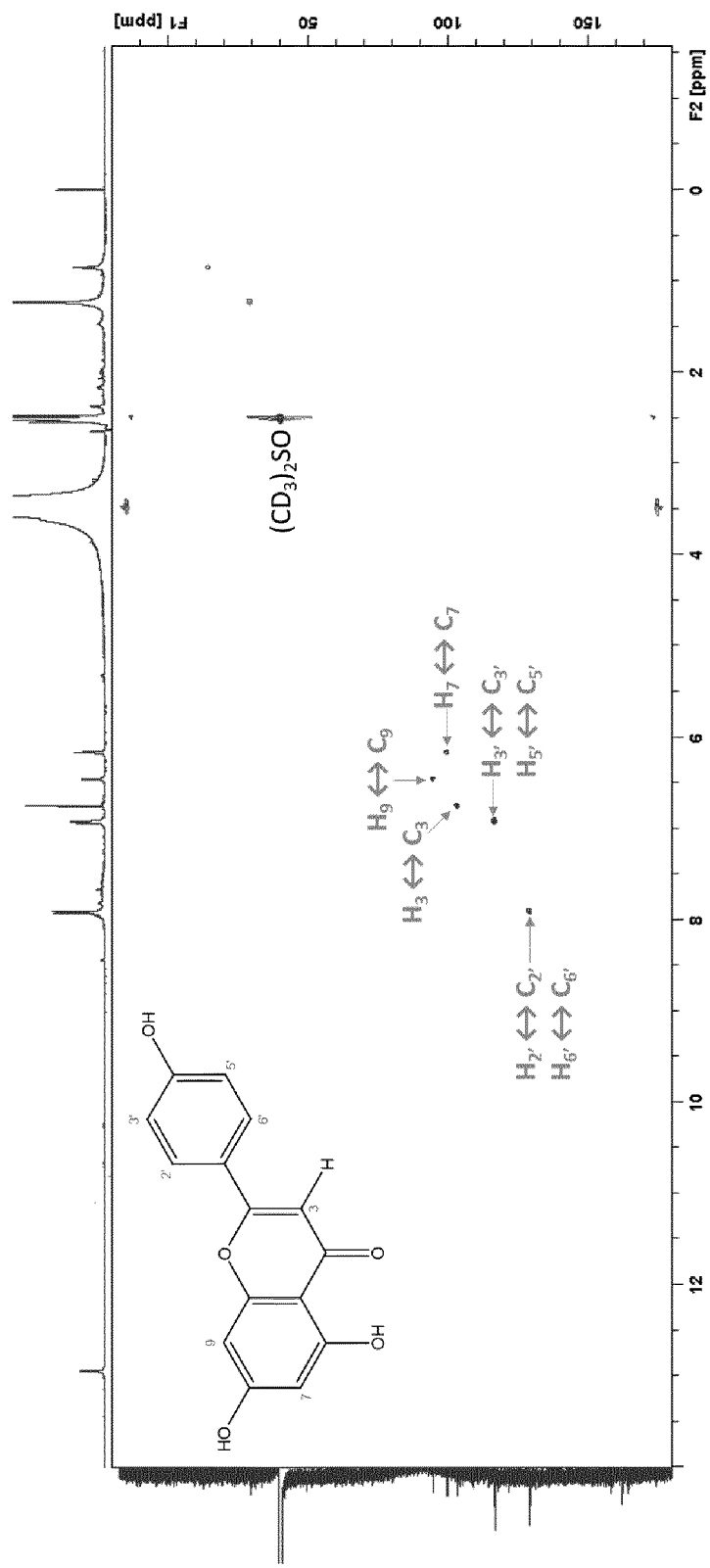
Figure 6E:
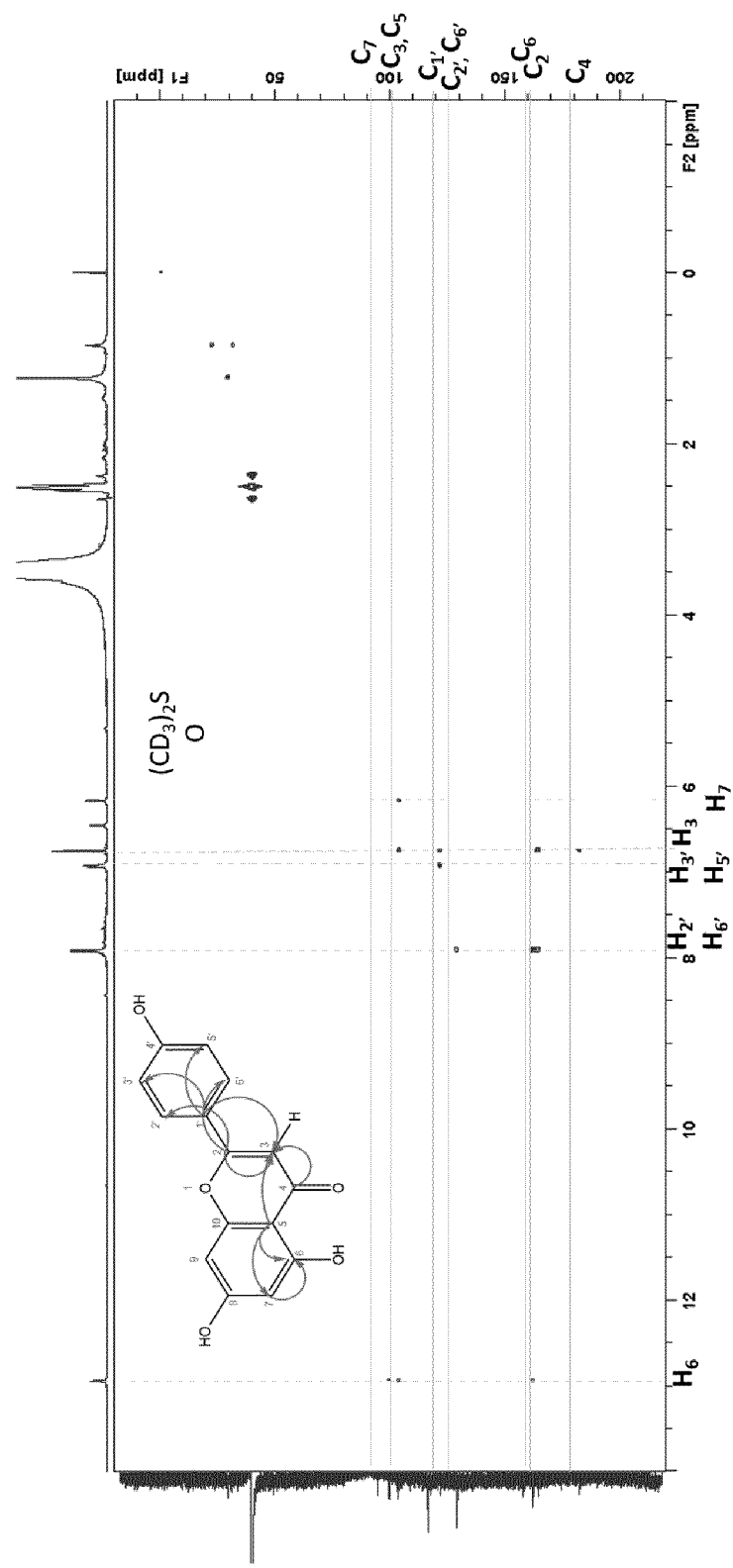
Figure 7A:
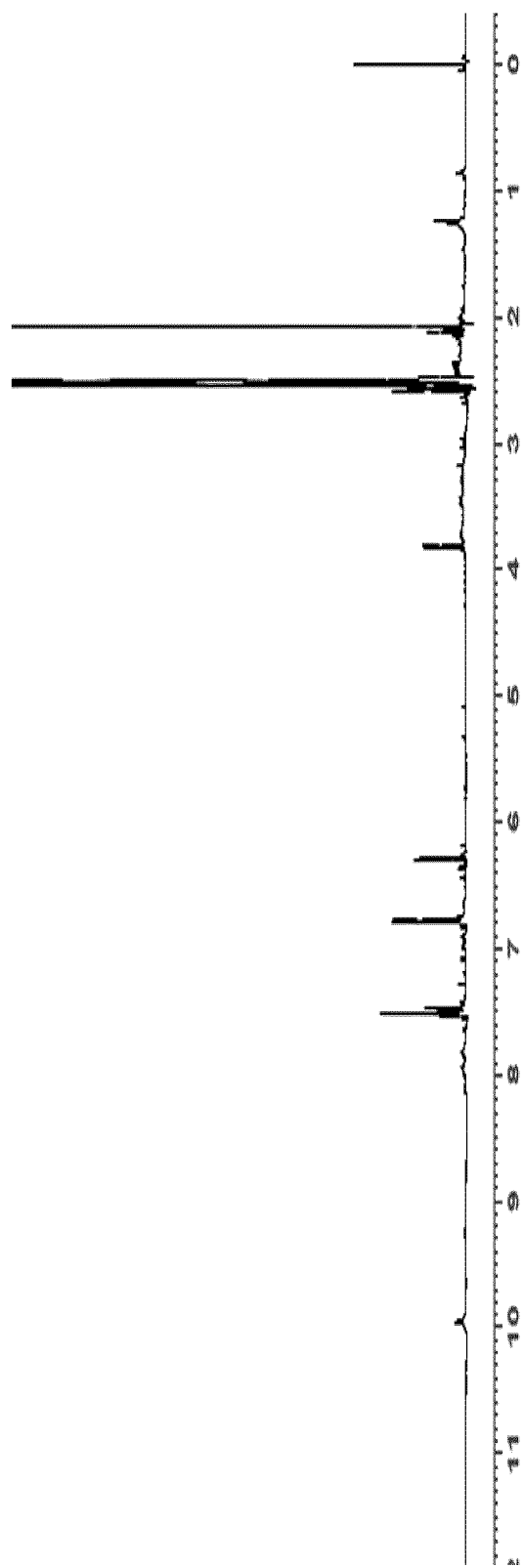
FIGS. 7a, 7b, 7c, 7d and 7e represent the $^1$H, $^{13}$C, COSY, HSQC and HMBC NMR spectra of para-coumaric acid, isolated from sample E2.
Figure 7B:
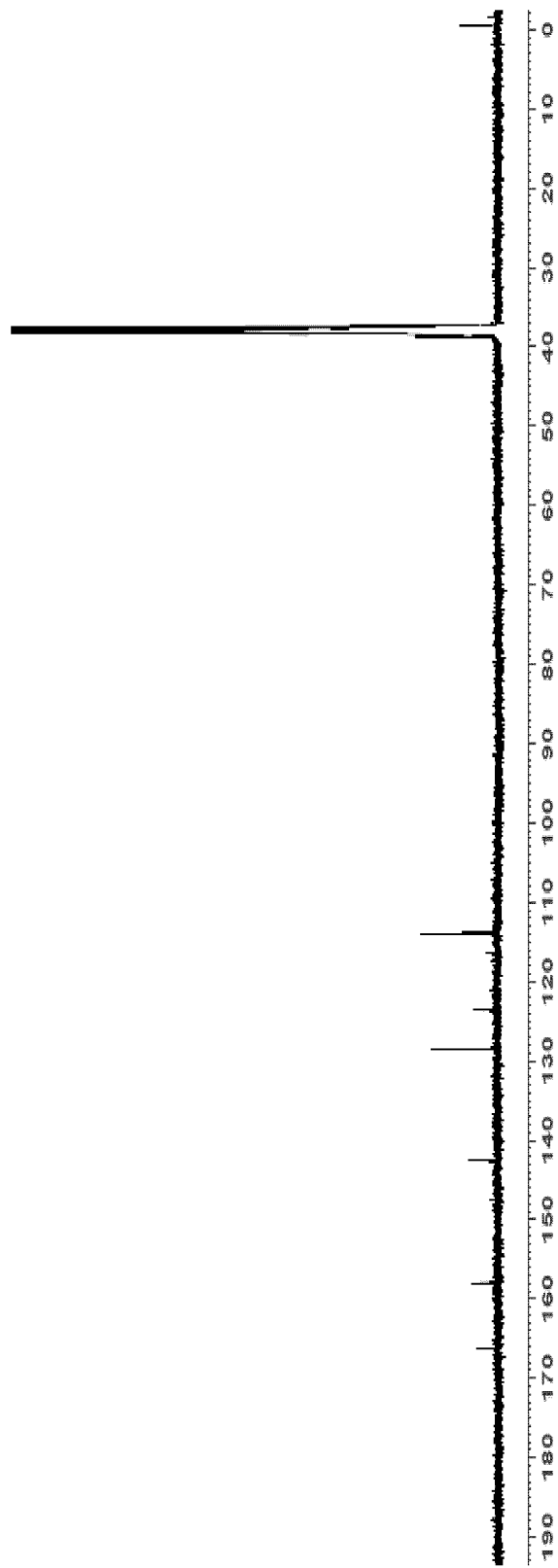
Figure 7C:
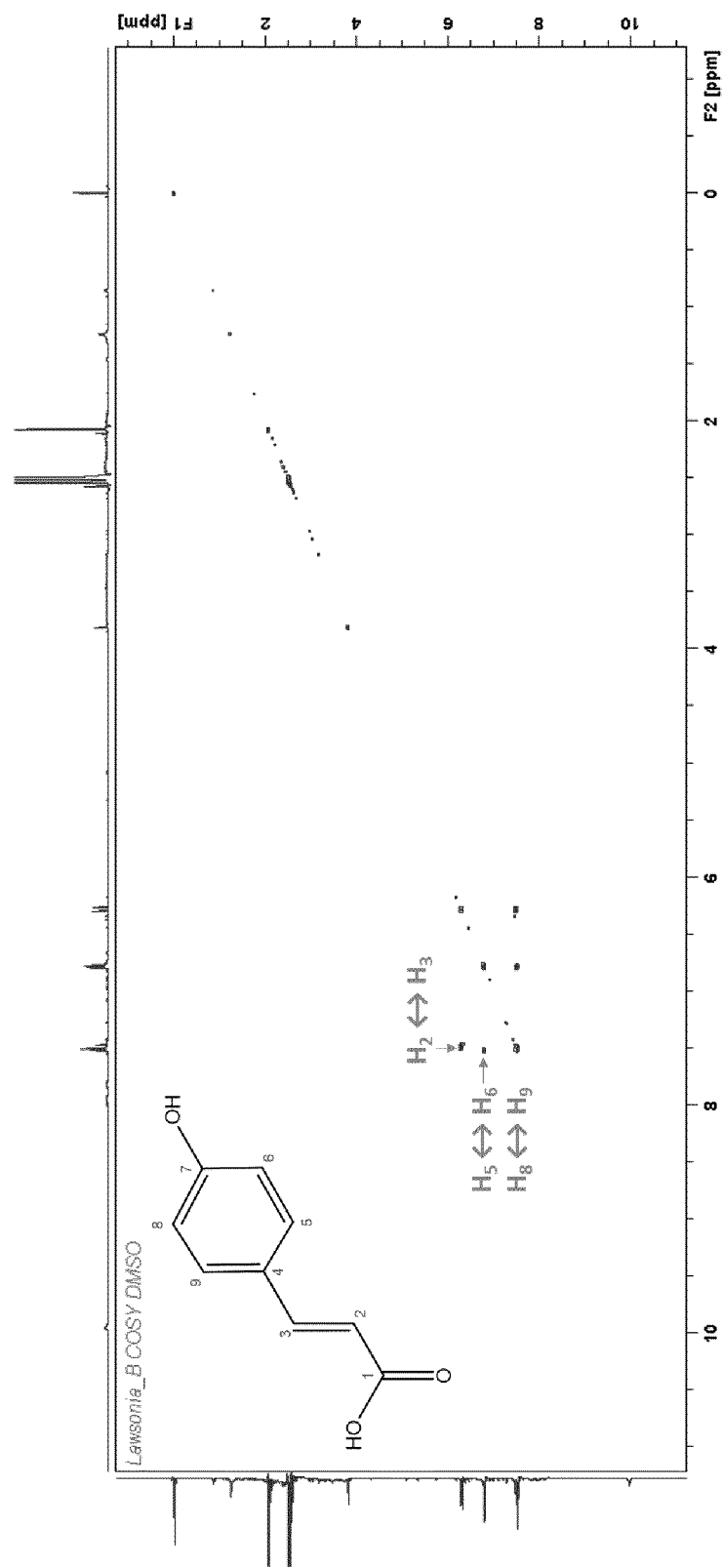
Figure 7D:
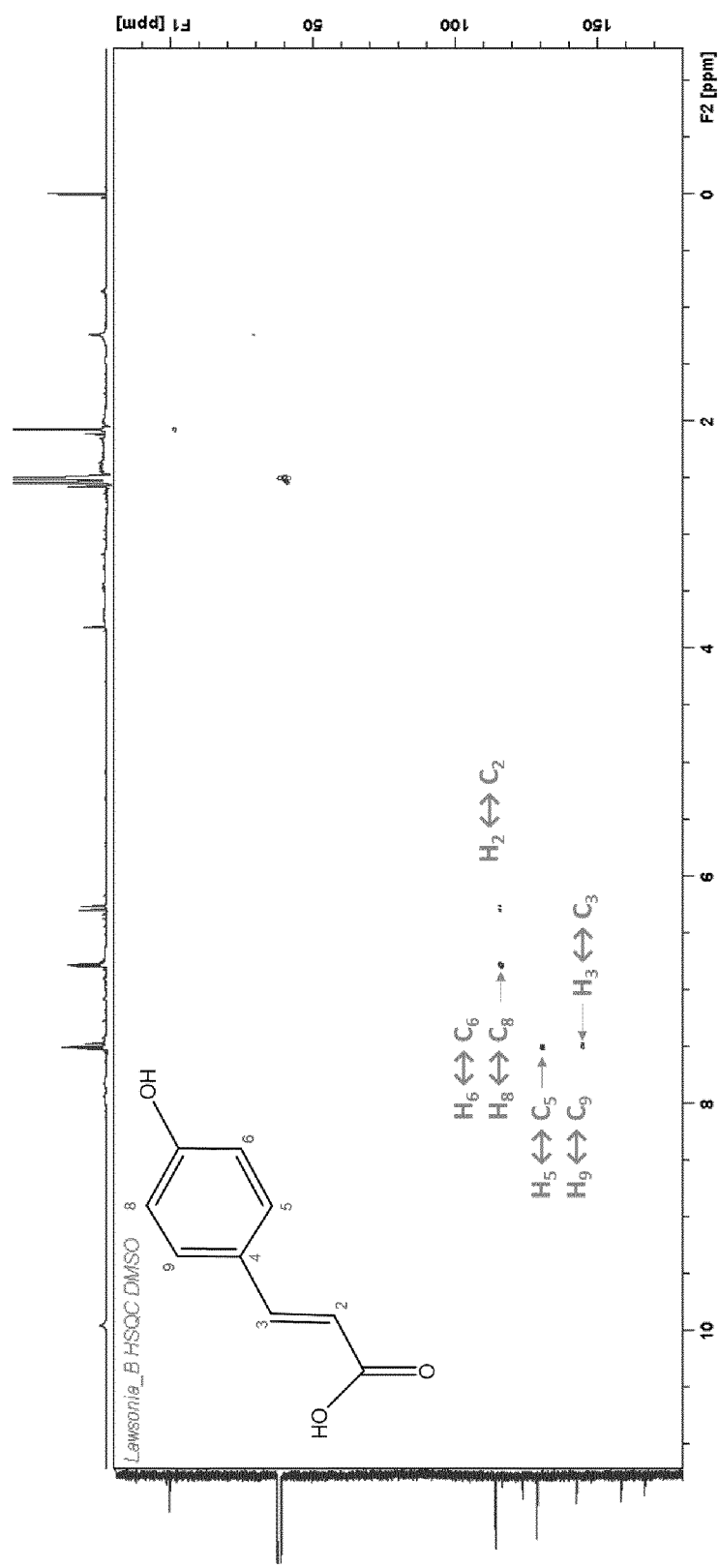
Figure 7E:
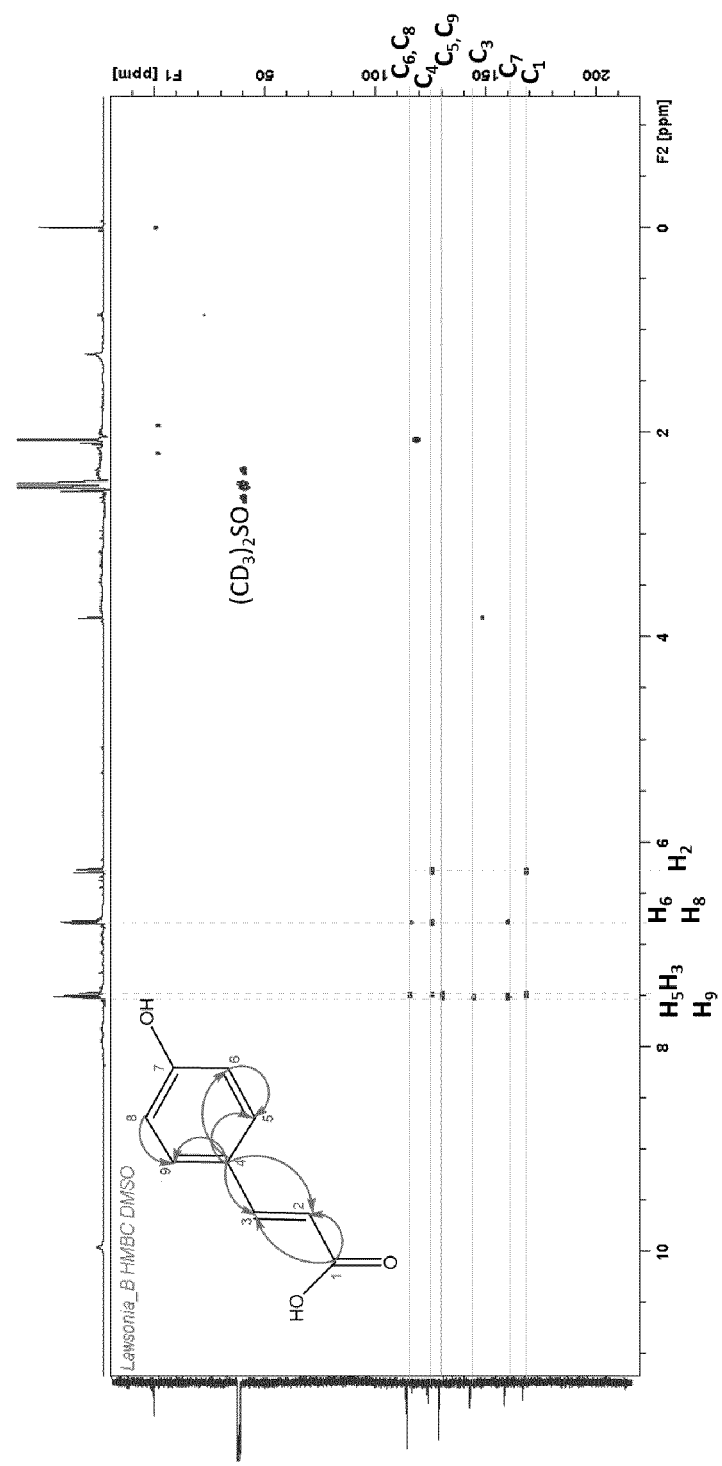

The obtained UHPLC-UV chromatogram is displayed in FIGS. 1 and 2. The peaks that can be observed on a zoom of said chromatogram (FIG. 2, plain line) have been associated with the following compounds:

| 15 |
|---|
| lawsone |

| 1 | 2 |
|---|---|
| gallic acid | lalioside |
| 3 | 4 |
| myrciaphenone A | catechin |
| 5 | 6 |
| 2,3,4,6-tetrahydroxyacetophenone | 1,2-dihydroxy-4-O-glycosyloxynaphtalene |
| 7 | 10 |
| luteolin-4'-O-glucoside | para-coumaric acid |
| 11 | 12 |
| apigenin-7-O-β-glucoside | luteolin-3'-O-glucoside |
| 13 | 14 |
| apigenin-4'-O-β-glucoside | 3,4,5-trihydroxyacetophenone |
| 19 | 20 |
| 3',4',5,7-tetrahydroxyflavanone | luteolin |

| 15 |
| --- |
| lawsone |

| 21 | 22 |
| --- | --- |
| 3',5,7-trihydroxy-4'-methylflavone | apigenin |

UV Spectra

The UV spectra of the compounds corresponding to peaks No 15, 20, 22, 10 and 5 are displayed in FIGS. 3a, 3b, 3c, 3d and 3e respectively.

NMR Spectra

Peak 15

The $^1$H, $^{13}$C, COSY, HSQC and HMBC NMR spectra of the compound corresponding to peak 15 are displayed in FIGS. 4a, 4b, 4c, 4d and 4e.

Said compound has been identified as lawsone.

Indeed, the following attribution can be made with respect to the $^1$H and $^{13}$C NMR spectra:

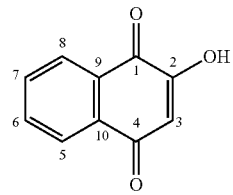

| Position | $^1$H-NMR (500 MHz, CDCl$_3$) | $^{13C}$-NMR (125 MHz, CDCl$_3$) |
| --- | --- | --- |
| 1 | — | 181.74 |
| 2 | 11.7, se | 160.02 |
| 3 | 5.8, s | 111.49 |
| 4 | — | 181.74 |
| 5 | 8.01, d, 7.1 | 126.45 |
| 6 | 7.83, m | 134.98 |
| 7 | 7.83, m | 133.79 |
| 8 | 7.95, d, 7.2 | 125.95 |
| 9 | — | 131.10 |
| 10 | — | 132.38 |

HRMS (ESI−) calcd for C10H5O3 [M−H]−: 173.0239, found: 173.0244 (0.5 mDa/2.9 ppm)

HRMS (ESI+) calcd for $C_{10}H_7O_3$ [M+H]+: 175.0395, found: 175.0405 (1.0 mDa/5.7 ppm)

Peak 20

The $^1$H, $^{13}$C, COSY, HSQC and HMBC NMR spectra of the compound corresponding to peak 15 are displayed in FIGS. 5a, 5b, 5c, 5d and 5e.

Said compound has been identified as luteolin.

Indeed, the following attribution can be made with respect to the $^1$H and $^{13}$C NMR spectra:

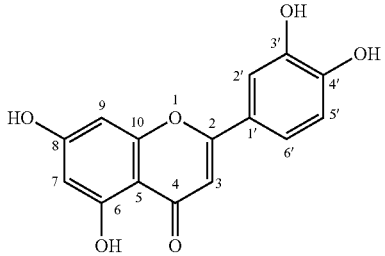

| Position | $^1$H-NMR (500 MHz, CDCl$_3$) | $^{13C}$-NMR (125 MHz, CDCl$_3$) |
| --- | --- | --- |
| 1 | — | — |
| 2 | — | 161.93 |
| 3 | 6.68, s | 103.32 |
| 4 | — | 182.12 |
| 5 | — | 104.15 |
| 6 | 12.99 se | 164.34 |
| 7 | 6.19, s | 99.28 |
| 8 | 10.86, se | 164.58 |
| 9 | 6.45, s | 94.29 |
| 10 | — | 157.74 |
| 1' | — | 121.95 |
| 2' | 7.40, d, 5 | 133.82 |
| 3' | 9.42, se | 146.19 |
| 4' | 9.44, se | 150.15 |
| 5' | 6.89, d, 9 | 116.47 |
| 6' | 7.43, d, 3 | 118.57 |

HRMS (ESI−) calcd for C15H9O6 [M−H]−: 285.0399, found: 285.0398 (0.1 mDa/0.4 ppm)

HRMS (ESI+) calcd for C15H11O6 [M+H]+: 287.0556, found: 287.0560 (0.4 mDa/1.4 ppm)

Peak 22

The $^1$H, $^{13}$C, COSY, HSQC and HMBC NMR spectra of the compound corresponding to peak 15 are displayed in FIGS. 6a, 6b, 6c, 6d and 6e.

Said compound has been identified as apigenin.

Indeed, the following attribution can be made with respect to the $^1$H and $^{13}$C spectra:

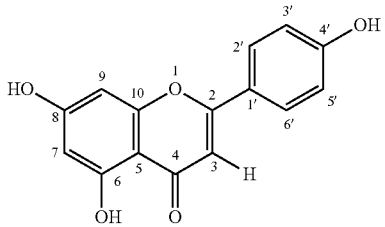

| Position | $^1$H-NMR (500 MHz, CDCl$_3$) | $^{13C}$-NMR (125 MHz, CDCl$_3$) |
| --- | --- | --- |
| 1 | — | — |
| 2 | — | 161.82 |
| 3 | 6.75, s | 103.25 |
| 4 | — | 182 |
| 5 | — | 103.25 |
| 6 | 12.95 se | 164.02 |
| 7 | 6.17, s | 99.52 |
| 8 | — | 164.17 |
| 9 | 6.46, s | 94.63 |
| 10 | — | — |
| 1' | — | 121.65 |
| 2' | 7.92, d, 9 | 128.91 |
| 3' | 6.93, d, 9 | 116.57 |
| 4' | — | 157.90 |

-continued

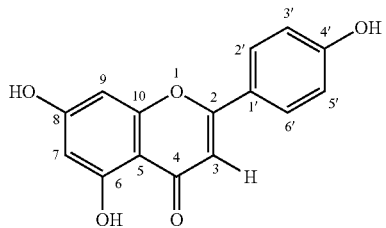

| Position | $^1$H-NMR (500 MHz, CDCl$_3$) | $^{13}C$-NMR (125 MHz, CDCl$_3$) |
|---|---|---|
| 5' | 6.93, d, 9 | 116.57 |
| 6' | 7.92, d, 9 | 128.91 |

HRMS (ESI−) calcd for C15H9O5 [M−H]−: 269.045, found: 269.0462 (1.2 mDa/4.5 ppm)

HRMS (ESI+) calcd for C15H11O5 [M+H]+: 271.0606, found: 271.0608 (0.2 mDa/0.7 ppm)

Peak 10

The $^1$H, $^{13}$C, COSY, HSQC and HMBC NMR spectra of the compound corresponding to peak 15 are displayed in FIGS. 7a, 7b, 7c, 7d and 7e.

Said compound has been identified as para-coumaric acid.

Indeed, the following attribution can be made with respect to the $^1$H and $^{13}$C spectra:

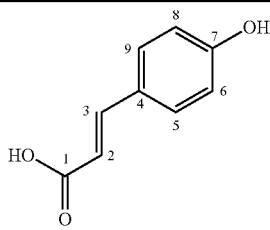

| Position | $^1$H-NMR (500 MHz, CDCl$_3$) | $^{13}C$-NMR (125 MHz, CDCl$_3$) |
|---|---|---|
| 1 | — | 166.28 |
| 2 | 6.29, d, 16 | 113.64 |
| 3 | 7.48, s | 142.51 |
| 4 | — | 123.58 |
| 5 | 7.52, d, 8.6 | 128.43 |
| 6 | 6.75, 8.6 | 114.06 |
| 7 | 9.96, se | 157.92 |
| 8 | 6.75, d, 8.6 | 114.06 |
| 9 | 7.52, d, 8.6 | 128.43 |

HRMS (ESI−) calcd for C9H7O3 [M−H]−: 163.0395, found: 163.0403 (0.8 mDa/4.9 ppm)

B) Quantitative Analysis

Material and Methods

Batches Samples

LP110: Ethyl acetate extract standardized with maltodextrine—industrial scale.

ES310: Ethyl acetate extract standardized with maltodextrine—laboratory scale.

JQ137A: Isopropyl acetate Henna extract with fructose—laboratory scale.

The lawsone in each of the above standardized extract is equal to 1.1 wt. %.

Experimental Conditions

Luteolin, apigenin were titrated by analytical HPLC performed with a C18 column (XBridge 100 C18; 3.5 mm, 150 mm×4.6 mm) using gradient conditions (see below) with H$_2$O/trifluoroacetic acid 0.1% (A) and Acetonitrile/trifluoroacetic acid 0.1% (B) as eluent:

Gradient conditions: t0 A 18% B 82%; t1 min: A 18% B 82%; 10 min A 50% B 50%; 10.1 min: A 18% B 82% UV detection is at 340 nm for apigenin and 310. Flow rate was 1 mL/min and temperature 40° C. Pure luteolin, apigenin and p-coumarin were used for calibration.

Results

| Sample | Mass (mg) | Vol (mL) | $V_{inj}$ (µg) | $Q_{inj}$(µg) luteolin | apigenin | P-coumaric acid |
|---|---|---|---|---|---|---|
| LP110 1 | 215.5 | 20 | 5 | 0.0951 | 0.0132 | 0.0234 |
| LP110 2 | 266.1 | 20 | 5 | 0.1191 | 0.0163 | 0.0281 |
| LP110 3 | 233.1 | 20 | 5 | 0.1029 | 0.0157 | 0.0256 |
| ES3310 4 | 265.8 | 20 | 5 | 0.2348 | 0.0484 | 0.0285 |
| ES3310 5 | 217.25 | 20 | 5 | 0.195 | 0.0285 | 0.0238 |
| ES3310 6 | 227 | 20 | 5 | 0.2376 | 0.0307 | 0.0262 |
| JQ137A 7 | 235.9 | 20 | 5 | 0.1015 | 0.0178 | 0.0159 |
| JQ137A 8 | 222.6 | 20 | 5 | 0.1039 | 0.0188 | 0.0161 |
| JQ137A 9 | 227.7 | 20 | 5 | 0.1158 | 0.0195 | 0.0176 |

| Extract | Mean content (wt. %) luteolin | apigenin | p-coumaric acid |
|---|---|---|---|
| LP110 | 0.18% | 0.03% | 0.04% |
| ES3310 | 0.38% | 0.06% | 0.04% |
| JQ137A | 0.19% | 0.03% | 0.03% |

III. Assay Methods

Method 1: Lawsone Assay by HPLC

This method can be applied for:

A. the assay of lawsone in an extract

B. the assay of the total lawsone present in the free form or form of glycosylated lawsone derivatives in the aerial parts of Lawsonia inermis, obtained by acid hydrolysis, and thus quantifying the lawsone potential in the plant, C. the assay of the lawsone formed by enzymes.

Reagents

Lawsone >97% (HPLC) SIGMA-ref: H46805

Dichloromethane for analyses.

Sulfuric acid for analyses.

Methanol for analyses.

HPLC-grade water.

HPLC-grade acetonitrile.

HPLC-grade trifluoroacetic acid.

HPLC Conditions

Column: XBridge C18, 3.5 µm, 4.6×150 mm Waters Furnace: 40° C.

Solvents: S-A: 0.1% trifluoroacetic acid in water. S-B: 0.1% trifluoroacetic acid in acetonitrile.

Gradient: T0 min 40% S-A; T 1 min 40% S-A; T 10 min 5% S-A; T 11 min 5% S-A; T 11.1 min 40% S-A.

Wavelength: X=278 nm.

Flow rate: 1 mL/min

Injection: 10 µL.

Sample Preparation:
For whole or roughly crushed leaves:
50 g of leaves are crushed then sieved through a 0.355 μm sieve.
For leaf powders:
Use 50 g of leaf powder as is.
Preparation of the Solutions
Control Solutions:
Lawsone solution at 0.3 mg/mL in 1/1 methanol/ethanol. Dilute to 1/10, 1/20, 1/100 in 1/1 methanol/water.
Test Solutions:
Test solution A (assay of the lawsone present in an extract)
Dissolve 50 mg of extract in 100 mL of 1/1 methanol/water.
Dissolve with ultrasound.
Filtration on Acrodisc GF GHP.
Inject 10 L.
Test solution B (assay of total lawsone)
Introduce 80 mg of leaf powder into a volumetric flask.
Add 50 mL of 2N $H_2SO_4$.
Heat to 97° C. for 30 min.
Let cool.
Add methanol qs 100 mL.
Filter the solution on Acrodisc GF GHP 0.45 μm.
Inject 10 μL of the filtrate.
Test solution C (assay of the lawsone formed by enzymes)
Introduce 80 mg of leaf powder into a volumetric flask.
Add into 50 mL of demineralized water.
Place in an ultrasound bath for 30 min between 30 and 40° C. Let cool.
Add methanol qs 100 mL.
Filter the solution on Acrodisc GF GHP 0.45 μm.
Inject 10 μL of the filtrate.
Results
Use the regression line calculated with the control solutions to determine:
A. the lawsone content of the extract,
B. the total lawsone content, and/or
C. the content in lawsone formed by the enzymes.
Method 2: Assay of Nitrogen-Containing Compounds (Amino Acids, Proteins
Free amino acids and proteins can be assayed before or after hydrolysis by ninhydrin spectrophotometry. The results are expressed in percentage of amino acids relative to asparagine.
Assay of Total Proteins and Amino Acids
Principle
Colorimetric assay of amino acids by the ninhydrin reagent after acid hydrolysis. The results are expressed in percentage of total amino acids relative to asparagine.
Reagents
Citrate Buffer (pH=5)
Dissolve 2.1 g of citric acid in 20 mL of water, add 20 mL of 1 N sodium hydroxide and adjust to 50 mL with water.
Ninhydrin Reagent:
Dissolve 0.08 g of tin (II) chloride ($SnCl_2$, $2H_2O$) in 50 ml of citrate buffer (pH=5).
Dissolve 2 g of ninhydrin in 50 mL ethylene glycol monomethyl ether (EGME).
Mix the two solutions.
6N Hydrochloric Acid
Dilute to ½ of concentrated hydrochloric acid (36%).
Diluent
Mix 100 mL of 1-propanol with 100 mL of water.
Preparation of the Solutions
Preparation of the Calibration Range
Dissolve 17 mg of asparagine in 100 mL of water.

Preparation of the Test Solutions
Weigh approximately 30 to 200 mg of extract depending on the sample to analyze (pet) in a screw thread tube, add 2 mL of 6N HCl.
Hermetically seal then place for around 16 hours at 110° C. Neutralize with 3N sodium hydroxide (methyl red changes color) then adjust to 20 ml with water.
Assay

|  | T 0.1 | T 0.2 | T 0.5 | Test | Blank |
|---|---|---|---|---|---|
| Control solution (mL) | 0.1 | 0.2 | 0.5 | — | — |
| Test solution (mL) | — | — | — | 0.2 | — |
| Water (mL) | 1 | 1 | 1 | 1 | 1 |
| Ninhydrin reagent (mL) | 1 | 1 | 1 | 1 | 1 |

Stir and place in a water bath at 100° C. for 20 minutes.
Cool in an ice bath.
Adjust to 10 ml with diluent.
Measure the absorbance at 570 nm of the different solutions against the blank.
Calculations
Construct the calibration curve.
Deduce from it the total amino acid concentration ($Q_{AAT}$), expressed in asparagine, in the test solutions.
The total amino acid content ($T_{AAT}$) of the extract is given by the following formula:

$$T_{AAT}(\%) = \frac{Q_{AAT} \times 100 \times 20}{pe_1}$$

with:
$Q_{AAT}$ in mg/ml
$pe_1$ in mg
Method 3: Weight Assay of Chlorophylls
The chlorophyll content in the extract may be evaluated by the weight obtained after washing the extract with heptane. The extract is taken up by 10 V of methanol. After stirring for 15 min, the solution is filtered. The supernatant is dried and constitutes the fraction containing chlorophylls.

The invention claimed is:

1. An extract of aerial parts of *Lawsonia inermis* containing between 10 and 60% by weight of lawsone relative to the total weight of the dry extract, wherein a portion of the lawsone results from enzymatic hydrolysis of glycosylated lawsone derivatives, and wherein the extract further contains luteolin, apigenin, para-coumaric acid and 2,3,4,6-tetrahydroxyacetophenone.

2. The extract according to claim 1 containing not more than 2% by weight of proteins, peptides or amino acids relative to the total weight of the dry extract.

3. A composition comprising the extract of claim 1 and a carrier, wherein the composition contains between 0.6 and 1.4 wt. % of lawsone relative to the total weight of the composition wherein said standardized dry extract contains between 0.6 and 1.4 wt. % of lawsone, and wherein:
the luteolin content is comprised between 0.05 and 1.0 wt. %,
the apigenin content is comprised between 0.01 and 0.5 wt. %, and the para-coumaric acid content is comprised between 0.01 and 0.5 wt. % relative to the total weight of the composition.

4. A preparation method for a lawsone extract comprising the following steps:
   a) macerating the aerial parts of *Lawsonia inermis* in water, at a pH between 4 and 8 to partially or totally hydrolyze enzymatically the glycosylated lawsone derivatives, initially present in the aerial parts of *Lawsonia inermis* and to provide an aqueous solution containing lawsone;
   b) adding an organic solvent to the solution obtained from step a), the miscibility with water of said solvent being less than 10% by weight at 25° C., to form an aqueous phase and an organic phase;
   c) recovering the organic phase obtained from step b); and
   d) concentrating the organic phase recovered from step c), to obtain a lawsone—rich extract.

5. The preparation method according to claim 4, wherein the water temperature during step a) is comprised between 20° C. and 60° C.

6. The preparation method according to claim 4, wherein step a) is carried out at a pH between 5 and 7.5.

7. The preparation method for a lawsone—rich extract according to claim 4, wherein it does not include any step of changing the pH of the aqueous solution or the aqueous phase by addition of acid or base.

8. The preparation method for a lawsone—rich extract according to claim 4, wherein step a) is carried out under stirring, and the duration of the maceration is comprised between 15 minutes and 2 h.

9. The preparation method for a lawsone—rich extract according to claim 4, wherein in step a), the volume of water used is 5 to 15 times greater than the mass of the aerial parts of *Lawsonia inermis* subjected to maceration.

10. The preparation method according to claim 4, wherein the organic solvent added during step b) is characterized by a dipole moment less than 2.0 D, and is selected from the group consisting of alcohols, chlorinated solvents, ketones, ethers, esters and their mixtures.

11. The preparation method according to claim 4, wherein the organic solvent is a $(C_1-C_6)$ alkyl acetate or a mixture of $(C_1-C_6)$ alkyl acetates.

12. The preparation method according to claim 4, wherein the lawsone—rich extract obtained from step d) contains more than 50% of the lawsone initially present in the free form or in the form of glycosylated lawsone derivatives, in the aerial parts of *Lawsonia inermis* subjected to maceration in step a).

13. The preparation method according to claim 4 further comprising the step of:
   c') adding a carrier between steps c) and d), and
   e) drying after step d) to obtain a standardized dry extract.

14. An extract that can be obtained by the method according to claim 4.

15. A cosmetic dye composition comprising an extract according to claim 1 and at least one cosmetically—acceptable excipient.

16. A standardized dry extract that can be obtained by the method according to claim 13.

17. A cosmetic dye composition comprising a standardized dry extract according to claim 3 and at least one cosmetically—acceptable excipient.

18. A cosmetic dye composition comprising a standardized dry extract that can be obtained by the method according to claim 13, and at least one cosmetically—acceptable excipient.

* * * * *